(12) United States Patent
Timmerman

(10) Patent No.: US 8,575,319 B2
(45) Date of Patent: Nov. 5, 2013

(54) CLEAVABLE VACCINE COMPOSITIONS AND USES THEREOF AND METHODS OF MAKING AND USING THE SAME

(75) Inventor: John M. Timmerman, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 821 days.

(21) Appl. No.: 12/281,229

(22) PCT Filed: Mar. 9, 2007

(86) PCT No.: PCT/US2007/006210
§ 371 (c)(1),
(2), (4) Date: Aug. 29, 2008

(87) PCT Pub. No.: WO2007/106435
PCT Pub. Date: Sep. 20, 2007

(65) Prior Publication Data
US 2009/0017060 A1    Jan. 15, 2009

Related U.S. Application Data

(60) Provisional application No. 60/781,293, filed on Mar. 10, 2006, provisional application No. 60/832,439, filed on Jul. 21, 2006.

(51) Int. Cl.
*C07K 16/00* (2006.01)

(52) U.S. Cl.
USPC .................................. 530/391.1; 424/178.1

(58) Field of Classification Search
None
See application file for complete search history.

(56) References Cited

U.S. PATENT DOCUMENTS

| 4,433,059 A * | 2/1984 | Chang et al. ............... 436/512 |
| 4,638,049 A | 1/1987 | Masuho et al. |
| 4,839,295 A | 6/1989 | Smith |
| 5,708,146 A | 1/1998 | Willner et al. |
| 6,132,718 A * | 10/2000 | Hansen ..................... 424/131.1 |

OTHER PUBLICATIONS

Kirkley et al, Immunobiology, 2001, 203:601-615).*
Betting et al, Blood, Nov. 2005, 106:427A.*
Bendandi, Nature Med, 1999, 5:1171-1171.*
Kwak, N Engl J Med, 1992, 327:1209-1215.*
Van Dijk-Wolthuis, et al. (1999) "A Versatile Method for Conjugation of Proteins and Peptides to Poly[-(dimethylamino)ethyl methacrylate]" Bioconjugate Chem. 10, 687-692.
International Search Report and Written Opinion received in PCT/US07/06210. Mailed Jan. 14, 2008.
Francis, M.J., et al. (1989) "Neutralizing Antibodies to All Seven Serotypes of Foot-and-Mouth Disease Virus Elicited by Synthetic Peptide" J. Immunology 69:171-176.
Timmerman, J., et al. (2000) "Linkage of Foreign Carrier Protein to a Self-Tumor Antigen Enhances the Immunogenicity of a Pulsed Dendritic Cell Vaccine" J. Immunology. 4797-4803.
Weng, W., et al. (2004) "Clinical Outcome of Lymphoma Patients after Idiotype Vaccination is Correlated with Humoral Immune Response and Immunoglobulin G Fc Receptor Genotype" J. Clinical Oncology 22:4717-4724.
Ronco, J., et al. (1991) "Induction of HIV-1 Neutralizing Antibodies by Synthetic Peptides" Vaccines 91:29-35.
Hsu, F. et al. (1997) "Tumor-Specific Idiotype Vaccines in the Treatment of Patients with B-Cell Lymphoma—Long-Term Results of a Clinical Trial" Blood 89(9):3129-3135.
Schaaper, W.M.M., et al. (1989) "Manipulation of Antipeptide Immune Response by Varying the Coupling of the Peptide with the Carrier Protein" Molecular Immunology 26(1): 81-85.

* cited by examiner

*Primary Examiner* — Mark Halvorson
(74) *Attorney, Agent, or Firm* — Suzannah K. Sundby, Esq.; Smith, Gambrell & Russell, LLP

(57) ABSTRACT

The invention relates to methods for making vaccines using linkages that are cleavable under lysosomal processing conditions, and vaccine compositions obtained therefrom. In some embodiments, the vaccines comprise a tumor antigen, an immunogenic carrier and a linker covalently linking the tumor antigen and the immunogenic carrier by a thio ether linkage. Vaccines of preferred embodiments can be used against a cellular proliferative disease that is characterized by the tumor antigen.

16 Claims, 15 Drawing Sheets

Figure 1:
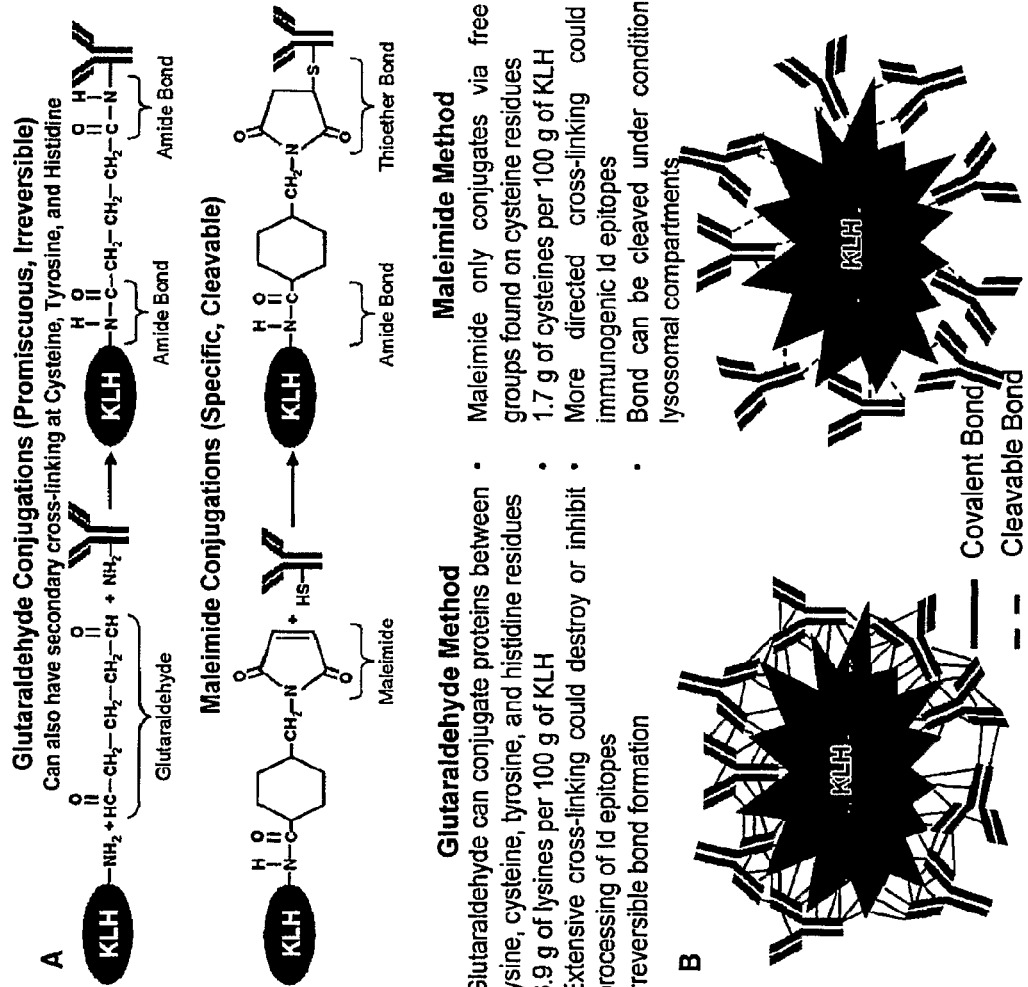

CLEAVABLE VACCINE COMPOSITIONS AND USES THEREOF AND METHODS OF MAKING AND USING THE SAME

1. CROSS-REFERENCE TO RELATED APPLICATIONS

This application claims priority to U.S. Provisional Patent Application Ser. No. 60/781,293 filed Mar. 10, 2006; and also to U.S. Provisional Patent Application Ser. No. 60/832,439 filed Jul. 21, 2006, which are both incorporated by reference in their entireties.

2. FIELD

The present disclosure relates to methods of making vaccines using linkages that are cleavable under lysosomal processing conditions, and vaccine compositions obtained therefrom. For example, cancer vaccines comprising a tumor antigen covalently linked to an immunogenic carrier by a thio ether linkage are disclosed.

3. BACKGROUND OF THE INVENTION

The treatment of cancer by immunization with tumor antigens is a promising new therapeutic approach which lacks the toxicities associated with traditional chemotherapy and radiotherapy (Blattman and Greenberg, *Science*, 305: 200-205, 2004.) Tumor antigen vaccination stimulates the host's own immune system to generate T cells and antibodies specific for tumor cells. It is being studied in a wide variety of human cancers, owing to the growing list of protein tumor antigens identified (Pardoll, *Nat Med*, 4: 525-531, 1998; Rosenberg, *Immunity*, 10: 281-287, 1999; Rosenberg, *Nature*, 411: 380-384, 2001). One tumor antigen reaching an advanced state of clinical development is the tumor-specific immunoglobulin clonally expressed by B cell lymphomas and related malignancies (Timmerman, *Int J Hematol*, 77: 444-455, 2003).

The collection of antigenic determinants in the variable region of an immunoglobulin is termed the idiotype (Id), and is unique for each lymphoma. Thus the idiotype of each B cell cancer can serve as a truly tumor-specific antigen, making it an attractive target for immunotherapy. The clonal T cell receptors expressed by T cell lymphomas express analogous structures that can also serve as targets for immunotherapy (Okada et al., *J Immunol*, 159: 5516-5527, 1997). Tumor-specific Id protein can be derived from individual B cell lymphomas using hybridoma (Levy and Dilley, *Proc Natl Acad Sci USA*, 75: 2411-2415, 1978) or molecular cloning techniques (Hawkins et al., *Blood*, 83: 3279-3288, 1994), yielding a custom-made tumor antigen for each patient. Vaccination with tumor-derived Id can potentially elicit a polyclonal antibody response, as well ad CD8+ and CD4+ T cells recognizing Id-derived peptides presented on class I and class II major histocompatibility complex proteins at the tumor cell surface (Timmerman, *Int J Hematol*, 77: 444-455, 2003; Hurvitz and Timmerman, *Expert Opin Biol Ther*, 5: 841-852, 2005).

To render this self-derived protein more recognizable to the immune system, Id is usually chemically conjugated to the highly immunogenic carrier protein keyhole limpet hemocyanin (KLH) using glutaraldehyde, as performed in numerous studies in both mouse models (Maloney et al., *Hybridoma*, 4: 191-209, 1985; Kaminski et al, *J Immunol*, 138: 1289-1296, 1987; George et al., *J Immunol*, 141: 2168-2174, 1988; Campbell et al., *J Immunol*, 139: 2825-2833, 1987; Campbell, M. J., et al., *J Immunol*, 145: 1029-1036, 1990; Campbell, et al., *J Immunol*, 141: 3227-3233, 1988; Kwak, L. W., et al., *Proc Natl Acad Sci USA*, 93: 10972-10977, 1996; Timmerman, J. M. and Levy, R., *J Immunol*, 164: 4797-4803, 2000) and humans (Kwak, L. W., et al., *N Engl J Med*, 327: 1209-1215, 1992; Kwak, L. W., et al., *Lancet*, 345: 1016-1020, 1995; Hsu, F. J., et al., *Nat Med*, 2: 52-58, 1996; Hsu, F. J., et al., *Blood*, 89: 3129-3135,1997; Bendandi, M., et al., *Nat Med*, 5: 1171-1177,1999; Timmerman, J. M., et al., *Blood*, 99: 1517-1526., 2002; Barrios, Y., et al., *Haematologica*, 87: 400-407, 2002; Timmerman, J. M., et al., *Blood*, 96: 578a, 2000; Timmerman, J., et al., *Blood*, 98: 341a (abstract#1440), 2001; Redfern, C., et al. Single agent activity of Favid [Id-KLH vaccine] for indolent NHL. *Blood*, 102: 898a (abstract #3341), 2003; Koc, O., et al. Id/KLH vaccine (Favid™) following treatment with rituximab: An analysis of response rate immprovement (RRI) and time-to-progression (TTP) in follicular lymphoma (FL). *Blood*, 104: 170a (abstract #587), 2004). Glutaraldehyde primarily cross-links proteins via lysine and cysteine residues, with secondary reactions at tyrosine and histidine (Migneault, I., et al., *Biotechniques*, 37: 790-796, 798-802, 2004).

The effectiveness of glutaraldehyde-conjugated Id-KLH protein vaccination in several murine lymphoma model systems (Kaminski, M. S., et al., *J Immunol*, 138: 1289-1296, 1987; George, A. J., et al., *J Immunol*, 141: 2168-2174, 1988; Campbell, M. J., et al., *J Immunol*, 139: 2825-2833, 1987) led to its adoption in Id vaccine clinical trials in patients with B cell lymphoma (Timmerman, J. M. and Levy, R. L., *Clinical Lymphoma*, 1: 129-139, 2000). In phase I/II trials in lymphoma, Id-KLH vaccination has been shown to elicit anti-Id immune responses that correlate with improved progression-free and overall survival, (Kwak, L. W., et al., *N Engl J Med*, 327: 1209-1215, 1992; Hsu, F. J., et al., *Blood*, 89: 3129-3135, 1997); clearance of circulating tumor cells from the blood (Bendandi, M., et al., Nat Med, 5: 1171-1177, 1999); and durable tumor regressions (Timmerman, J. M., et al., *Blood*, 99: 1517-1526, 2002; Redfern, C., et al., *Blood*, 102: 898a (abstract #3341), 2003; Koc, O., et al., *Blood*, 104: 170a (abstract #587), 2004). Based on these results, several large phase III clinical trials of Id-KLH vaccination are now underway in North America (Hurvitz, S. A. and Timmerman, J. M., *Curr Opin Oncol*, 17: 432-440, 2005.). These three trials, sponsored by Genitope (Redwood City, Calif.; WorldWideWeb.genitope.com), U.S. Pat. No. 5,972,334, Favrille (San Diego, Calif.; WorldWideWeb.favrille.com), U.S. Patent Publication US2005/0202004A1, and Accentia (Tampa, Fla.; WorldWideWeb.accentia.net), are all testing the efficacy of glutaraldehyde-conjugated Id-KLH co-administered with the cytokine granulocyte-macrophage colony stimulating factor (GM-CSF) after standard cytoreductive therapy.

Idiotype vaccination has shown promising results in phase I/II trials for non-Hodgkin's B cell lymphomas, and glutaraldehyde Id-KLH vaccines are now being formally evaluated for efficacy in several phase III clinical trials (Hurvitz, S. A. and Timmerman, *Curr Opin Oncol*, 17: 432440, 2005). Nonetheless, current Id-KLH vaccines remain far from optimal, as they fail in many patients to induce anti-Id immune responses, tumor regression, or prolonged survival. Glutaraldehyde Id-KLH conjugates fail to elicit anti-Id immune responses in up to one-half of vaccinated patients (Hsu, F. J., et al., *Blood*, 89: 3129-3135, 1997; Timmerman, J. M., et al., *Blood*, 96: 578a, 2000; Redfern, C., et al., *Blood*, 102: 898a (abstract #3341), 2003; Koc, O., et al., *Blood*, 104: 170a (abstract #587), 2004). Moreover, in some murine lymphoma models (A20), glutaraldehyde Id-KLH vaccines have been reported to lack anti-tumor efficacy (Biragyn, A. and Kwak, L. W. Models for Lymphoma. In: A. M. K. J. E. Coligan, D. H. Margulies, E. M. Shevach, W. Strober, and R. Coico, editors. (ed.), *Current Protocols in Immunology*, pp. 20.26.21-20.26.30. Hoboken, N.J.: John Wiley & Sons, Inc., 2001). Current clinical trials using glutaraldehyde to conjugate patient Id proteins to KLH may be limiting the effectiveness of the vaccines by over cross-linking the proteins.

Vaccines using other linking approaches would be desirable, with respect to both cancer vaccines and vaccines against other pathogens. Heterobifunctional cross-linking agents containing malemide have been used to link (1) enzymes or toxind to antibodies and antibody fragments and (2) peptides to proteins. (Hashida et al., *J Appl Biochem*, 6: 56-63, 1984; Peeters et al., *J Immunol Methods*, 120: 133-143, 1989; Yoshitake et al., *J Biochem (Tokyo)*, 92: 1413-1424, 1982; Yoshitake et al., *Eur J Biochem*, 101: 395-399, 1979). These methods generate a thio ether bond, which are disclosed in the art to be non-cleavable.

4. SUMMARY OF THE INVENTION

One aspect of the instant invention relates to methods of making vaccines. In some embodiments, the method involves providing a partially-reduced protein antigen, an immunogenic carrier, and a bifunctional linker having at least first and second reactive moieties; allowing conjuation of the linker to the immunogenic carrier and to the protein antigen under conditions which permit the formation of a covalent bond between the protein antigen and the first reactive moiety and a covalent bond between the immunogenic carrier and the second reactive moiety, wherein at least one of the covalent bonds so formed is cleavable under lysosomal processing conditions, and preferably the covalent bond between the protein antigen and the first reactive moeity.

In some embodiments, the partially-reduced protein antigen is obtained using one or more of the following reducing agents: dithiothrietol (DTT), 2-mercaptoethanol, 2-mercaptoethylamine, and/or other mild reducing agent. In some preferred embodiments the protein antigen is about 50% reduced. In more preferred embodiments, the partially-reduced protein antigen is maintained in a solution of phosphate-buffered saline and EDTA. Also, in some embodiments, the immunogenic carrier is first reacted with the linker and then conjugated to the partially-reduced protein antigen.

In some embodiments, one or more of the reactive moieties of the linker is maleimide and the covalent bond between the linker and protein antigen is a thio ether linkage. In some embodiments, the thio ether linkage is between the protein antigen (e.g., a tumor antigen) and the linker; whereas in some embodiments, the thio ether linkage is between the immunogenic carrier and the linker. In either case, in some embodiments, the other of the immunogenic carrier and antigen is covalently bonded to the linker via nitrogen.

The protein antigen can be a tumor antigen or a pathogenic antigen. For example, the protein antigen can be from a tumor-specific idiotypic protein, for example, an idiotypic protein derived from an idiotype-producing hybridoma and/or recombinantly generated using DNA. In some embodiments, an adjuvant is added, for example GM-CSF, a toll-like receptor (TLR) agonist, poly I:C, and/or CpG DNA.

The immunogenic carrier can be an immunogenic protein or glycoprotein, which is linked to the antigen to form a complex with superior immunogenic properties than the antigen alone. For example, the immuogenic carrier may be keyhole limpet hemocyanin (KLH), tetanus toxoid, *Klebsiella* ompA, and/or other immunogenic carrier proteins foreign to humans. In one preferred embodiment, the immunogenic carrier is keyhole limpet hemocyanin (KLH).

Another aspect of the instant invention relates to vaccines made by methods described herein. For example, some embodiments provide a cancer vaccine comprising: a tumor antigen; an immunogenic carrier; and a linker covalently linking the tumor antigen to the immunogenic carrier by a linker cleavable under lysosomal processing conditions. In some embodiments, the cancer vaccine elicits a protective immune response in more than about 50% of a vaccinated population. For example, using mice models, the vaccines described herein show protective immunity of more than about 50% of a population challenged with A20, 38C13, and BCL-1 lymphomas.

In some embodiments, the tumor antigen of the cancer vaccine is a peptide having 50 or more amino acids, while in some embodiments it is a protein. For example the tumor antigen may be at least one protein selected from tumor-specific idiotypic immunoglobulins, tumor-specific T-cell antigen receptors (TCRs), HER-2/neu, bcr/abl, p21ras, mutated p53, MAGE-1, MAGE-3, BAGE, GAGE, RAGE, MART-1/Melan-A, gp100, prostate-specific membrane antigen, prostate specific antigen, prostatic alkaline phosphatase, carcinoembryonic antigen, MUC-1, human papilloma virus E6 and E7, Epstein-Bar virus EBNA-1 and LMP-1, tyrosinase, telomerase reverse transcriptase (hTERT), and/or survivin. In a preferred embodiment, the protein is a tumor-specific idiotypic immunoglobulin, e.g., one associated with a B-cell proliferative disease, such as B-cell lymphoma, leukemia, multiple myeloma or light chain amyloidosis. In some embodiments, the protein is a T cell receptor (TCR), for example, a TCR associated with a T-cell proliferative disease, such as T-cell lymphoma or leukemia.

Still another aspect of the instant invention involves methods of treatment using one or more of the vaccines described herein. For example, some embodiments involve administering the vaccine in a therapeutic amount to a patient in need thereof. In some embodiments, e.g., in the case of some pathogen vaccines, the vaccine is administered prophylactically to a patient at risk of infection, or as part of a general immunization program. In other embodiments, e.g., in the case of some cancer vaccines, the vaccine is administered as part of a therapeutic treatment regimen, as described herein.

Preferred embodiments of the vaccines disclosed herein find use in treating a patient having a cancer expressing one or more of tumor-specific idiotypic immunoglobulins, tumor-specific T-cell antigen receptors (TCRs), HER-2/neu, bcr/abl, p21ras, mutated p53, MAGE-1, MAGE-3, BAGE, GAGE, RAGE, MART-1/Melan-A, gp100, prostate-specific membrane antigen, prostate specific antigen, prostatic alkaline phosphatase, carcinoembryonic antigen, MUC-1, human papilloma virus E6 and E7, Epstein-Bar virus EBNA-1 and LMP-1, tyrosinase, telomerase reverse transcriptase (hTERT), and/or survivin. In some embodiments, the patient has a B cell proliferative disease; in some embodiments, the patient has a T cell proliferative disease.

Preferably, the vaccines is administered via subcutaneous or intradermal injection. In some embodiments, the efficacy of the vaccine is independent of the duration of the conjugation step where the linker is attached to the protein antigen.

5. BRIEF DESCRIPTION OF THE DRAWINGS

FIG. 1. Comparison of glutaraldehyde and maleimide Id-KLH conjucation chemistries. (A) shows the bonds between the KLH and the antibody are amide bonds and that sulfo-SMCC forms an amide bond to KLH as with glutaraldehyde to form maleimide-activated KLH. The maleimide groups reacts with free sulfhydryl groups on the Id to form a thio ether bond. (B) shows a graphic depiction of predicted interactions between KLH and idiotype proteins via glutaraldehyde and maleimide methods.

Figure 2:
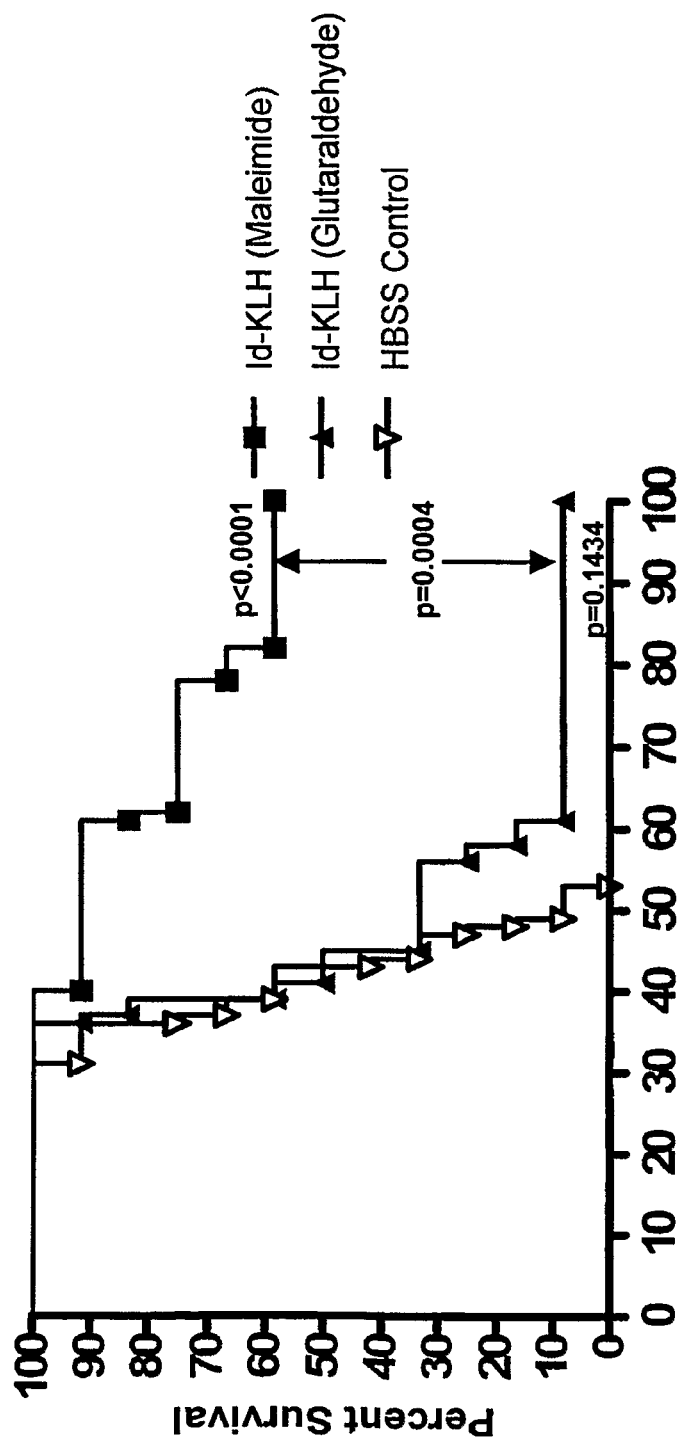

FIG. 2 Vaccination with Id-KLH maleimide conjugate successfully eradicates pre-established A20 murine B cell lymphoma. Groups of 12 BALB/c mice bearing s.c. A20 tumors established for 4 days were immunized with maleimide or gluraraldehyde Id-KLH plus GM-CSF weekly for 3 weeks.

Figure 3:
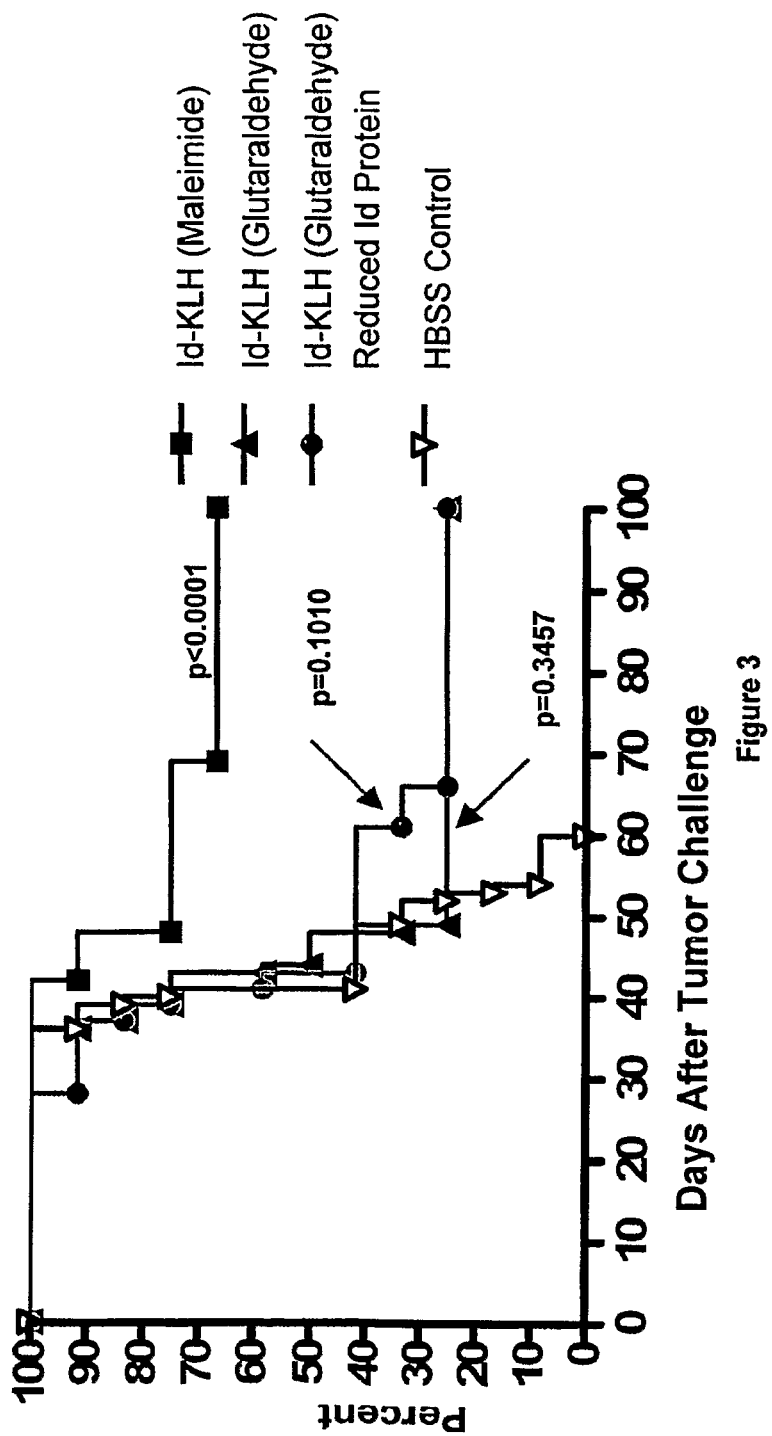

FIG. 3. Pre-reduction of the Id does not account for superior protection seen with maleimide Id-KLH over glutaradehyde conjugates. Groups of 12 BALB/c mice bearing s.c. A 20 tumors established for 4 days were treated with ID-KLH plus GM-CSF weekly for 3 weeks. Pre-reduced (as with maleimide) or native Id proteins were conjugated to KLH using glutaraldehyde.

Figure 4:
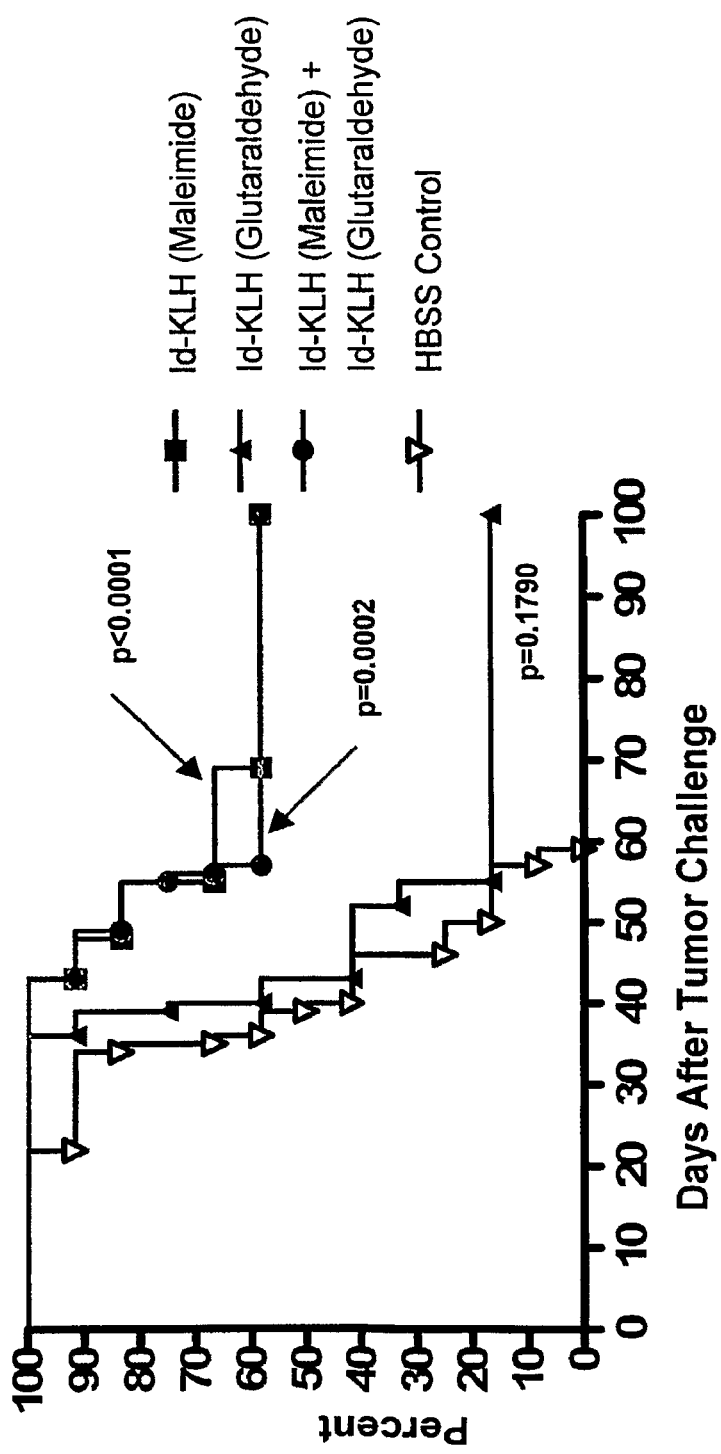

FIG. 4. Combination of Id-KLH maleimide and Id-KLH glutaraldehyde conjugates do not enhance anti-tumor immunity above that of maleimide Id-KLH alone. Groups of 12 BALB/c mice bearing s.c. A 20 tumors established for 4 days were treated with ID-KLH plus GM-CSF weekly for 3 weeks. A combination of 200 μg of Id-KLH protein (100 μg Id-KLH glutaraldehyde plus 100 μg Id-KLH maleimide) was compared to 100 μg of each protein alone.

Figure 5:
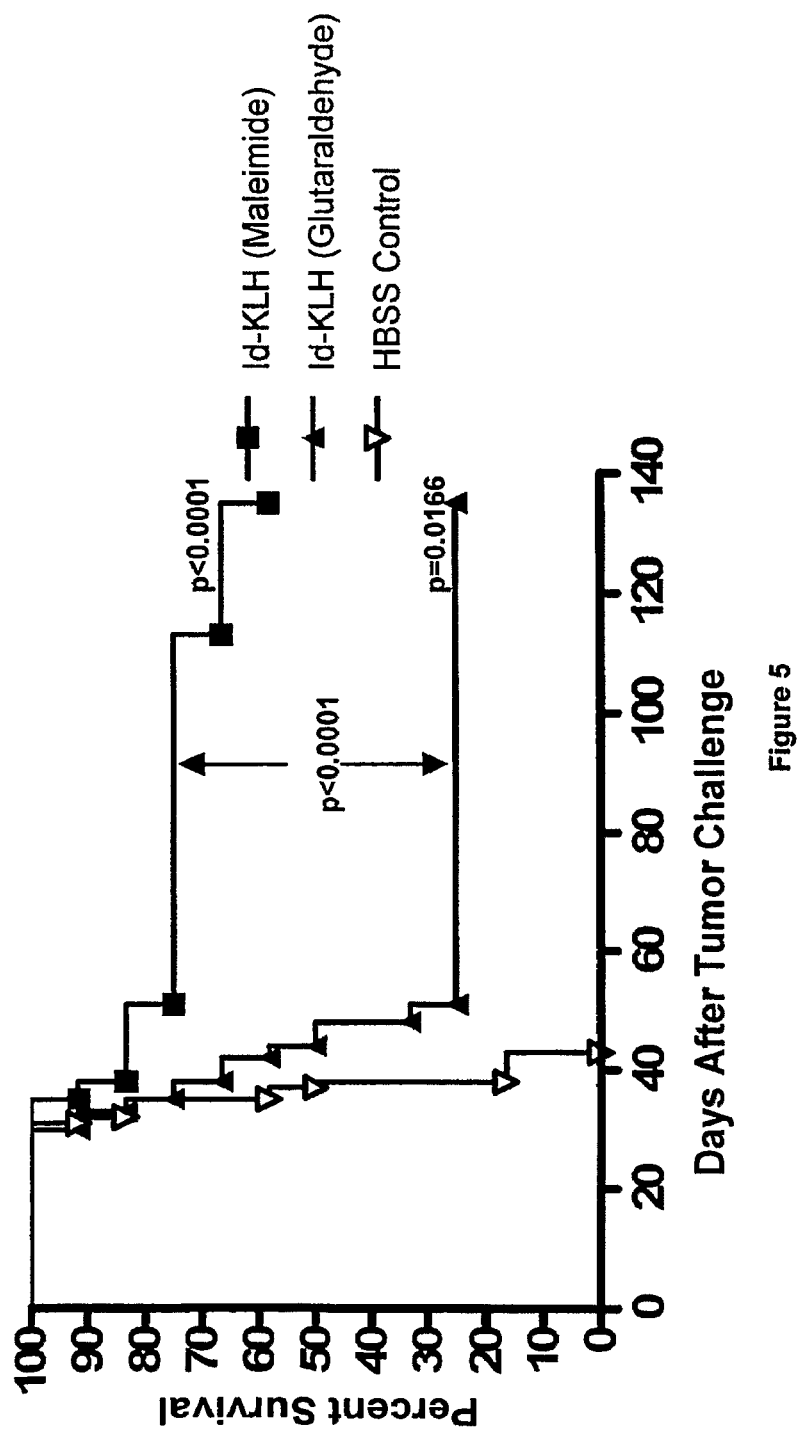

FIG. 5. A20 maleimide Id-KLH conjugate vaccines result in better tumor protection than glutaraldehyde Id-KLH. Groups of 12 BALB/c mice were treated with ID-KLH plus GM-CSF weekly for 3 weeks. Seven days after the final vaccination mice were challenged s.c. with A20 tumor.

Figure 6:
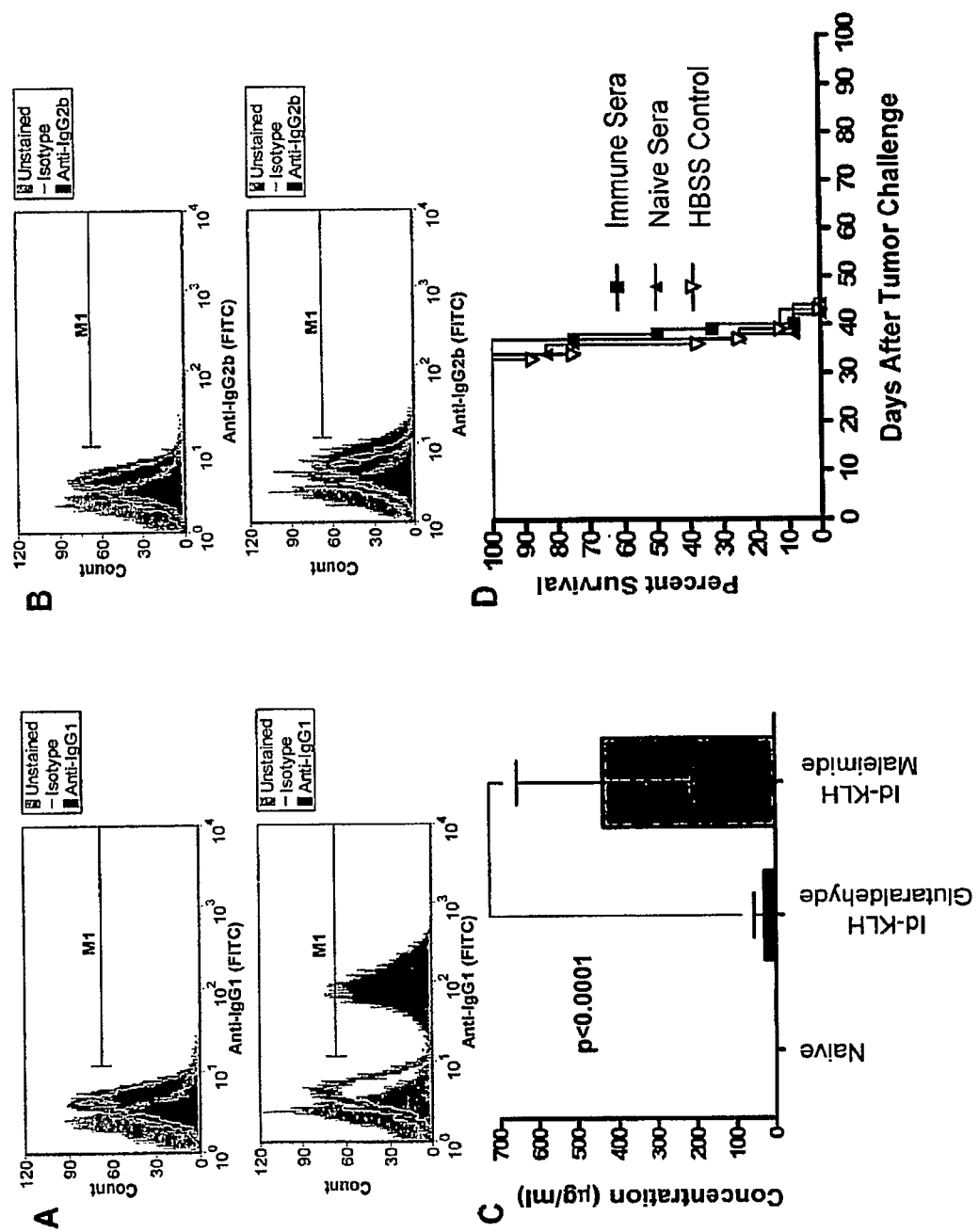

FIG. 6. Id-KLH maleimide conjugates yield superior anti-idiotype antibody titers, but antibodies are not required for effective anti-tumor immunity. (A) Anti-Id antibodies generated by maleimide Id-KLH conjugated recognize and bind to the surface of tumor cells. Naive and immune sera collected from mice treated with Id-KLH plus GM-CSF vaccines were used to stain A20 cells in vitro for IgG1 or (B) IgG2b. (C) Immune sera titers were determined by ELISA. (D) Passive transfer of maleimide Id-KLH immune serum does not protect against A20 lymphoma. Groups of 12 BALB/c mice were injected with A20 tumor cells i.p. Eight hours later mice were injected i.p. with immune sear, naïve sera, or HBSS.

Figure 7:
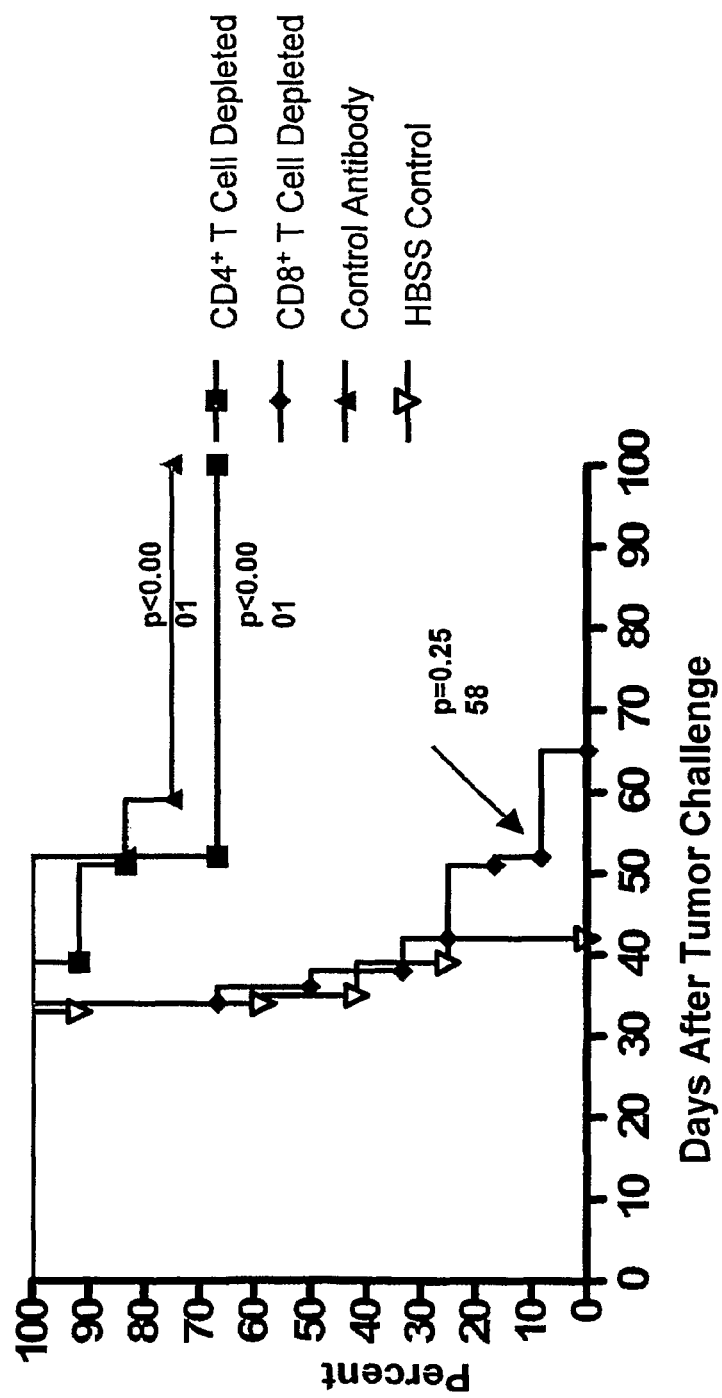

FIG. 7. CD8$^+$ T cells are important for A20 tumor protection after vaccination with Id-KLH maleimide conjugates. CD8$^+$ T cell depleted conditions failed to protect against A20 tumor challenge when compared with CD4$^+$ T cell depletion.

Figure 8:
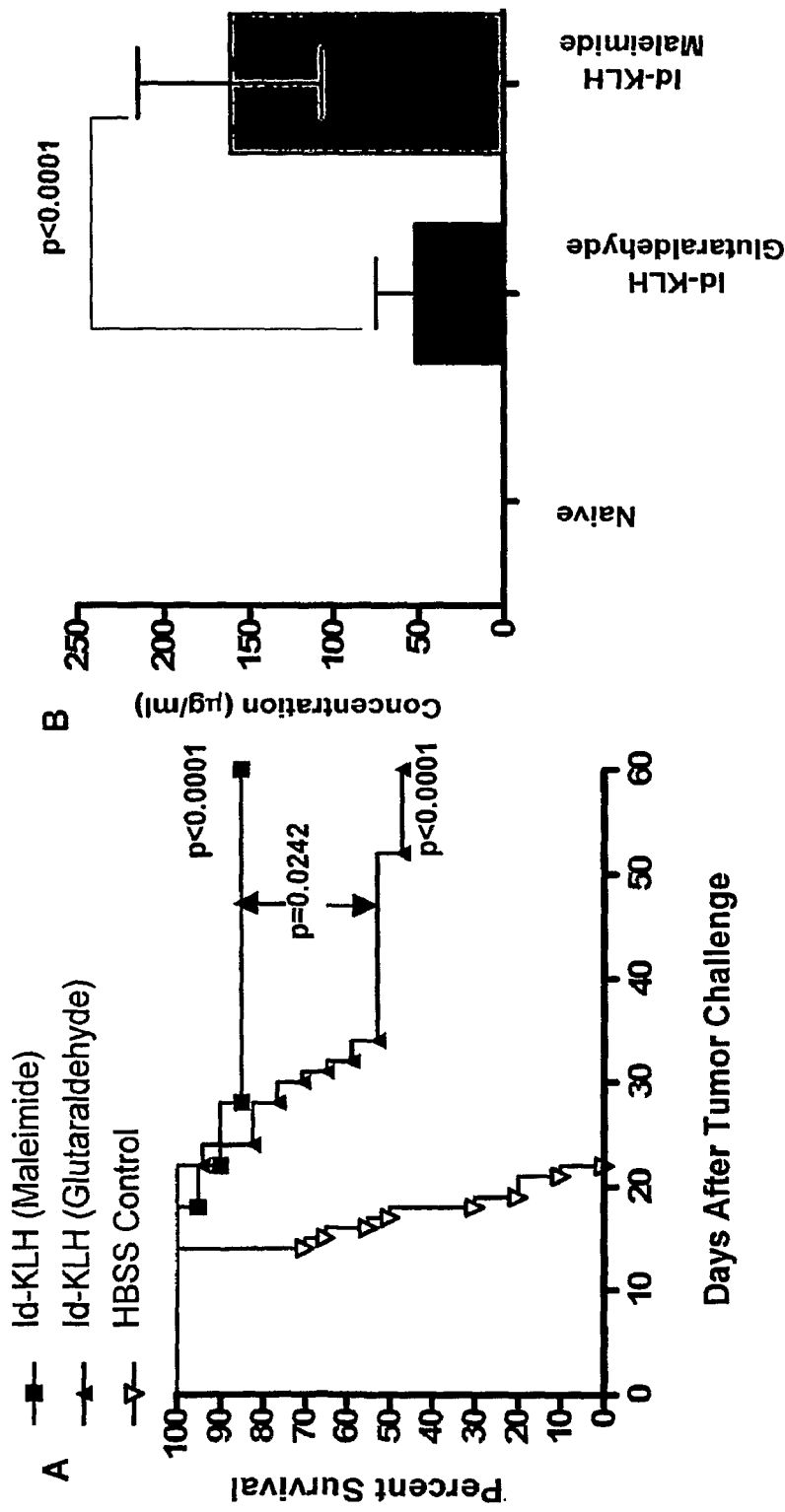

FIG. 8. Maleimide Id-KLH conjugate vaccines result in superior anti-tumor protection and higher anti-Id antibody titers than glutaraldehyde Id-KLH. (A) Groups of 12 C3H mice were treated with ID-KLH plus GM-CSF weekly for 3 weeks. Seven days after the final vaccination mice were challenged s.c. with 38C13 tumor. Analysis of pooled survival data from 2 separate 38C13 experiments. (B) Anti-Id antibody level in the serum of mice vaccinated with Id-KLH were determined 4 days prior to tumor challenge. Error bars indicate standard deviation. ** indicates a p-value of <0.0001 compared to glutaraldehyde Id-KLH conjugates.

Figure 9:
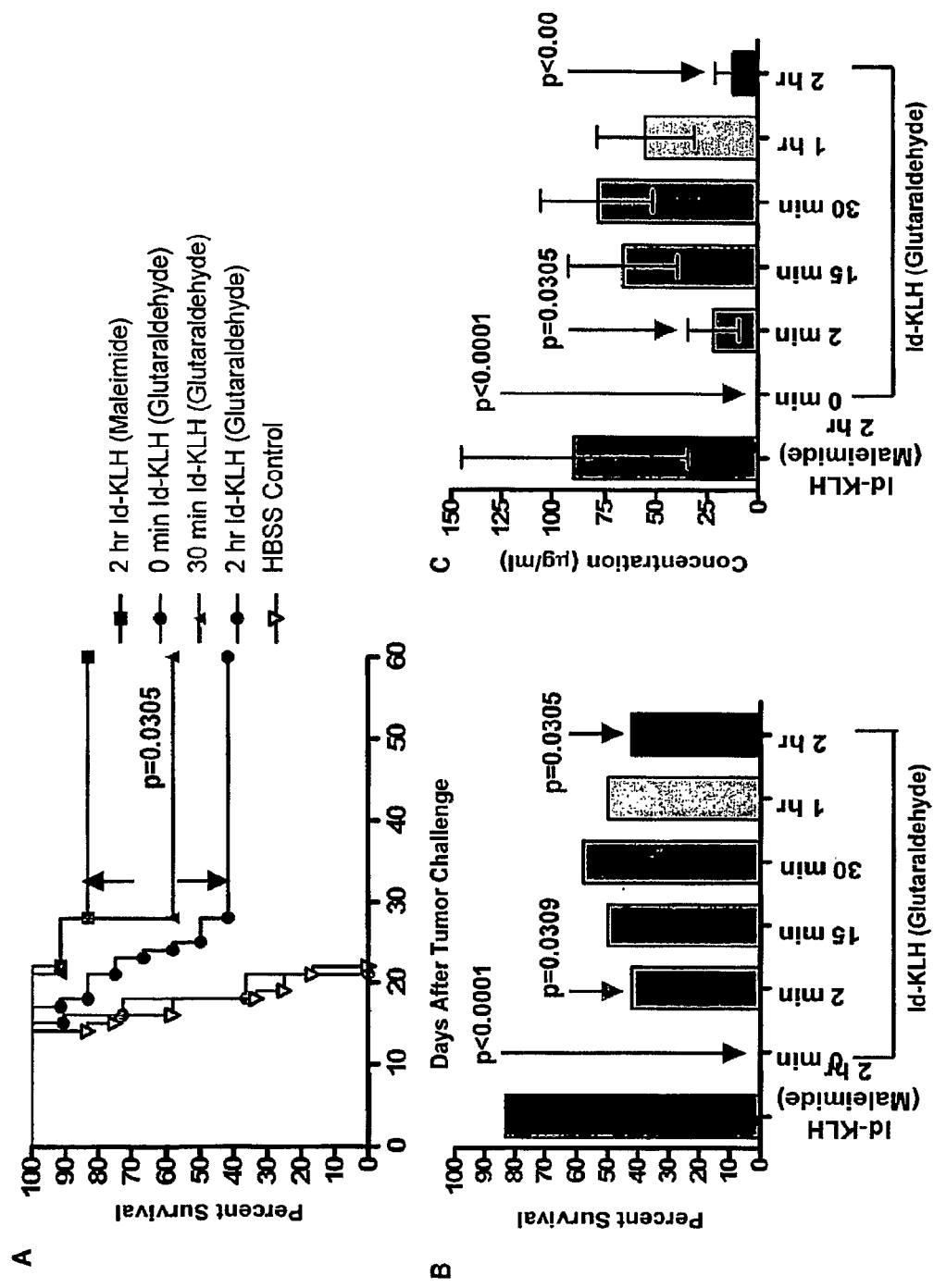

FIG. 9. The duration of glutaraldehyde conjugation critically affects the subsequent anti-tumor immune response. 38C13 Id was coupled to KLH using glutaraldehyde for various interval ranging from 2 minutes to 2 hours. (A-B) Groups of 12 C3H mice were treated with Id-KLH plus GM-CSF weekly for 3 weeks. Seven days after the final vaccination mice were challenged s.c. with 38C13 tumor. (C) Anti-Id antibody level in the serum of mice vaccinated with Id-KLH were determined 4 days prior to tumor challenge. ** indicates a p-value of <0.0001 compared to maleimide Id-KLH conjugates.

Figure 10:
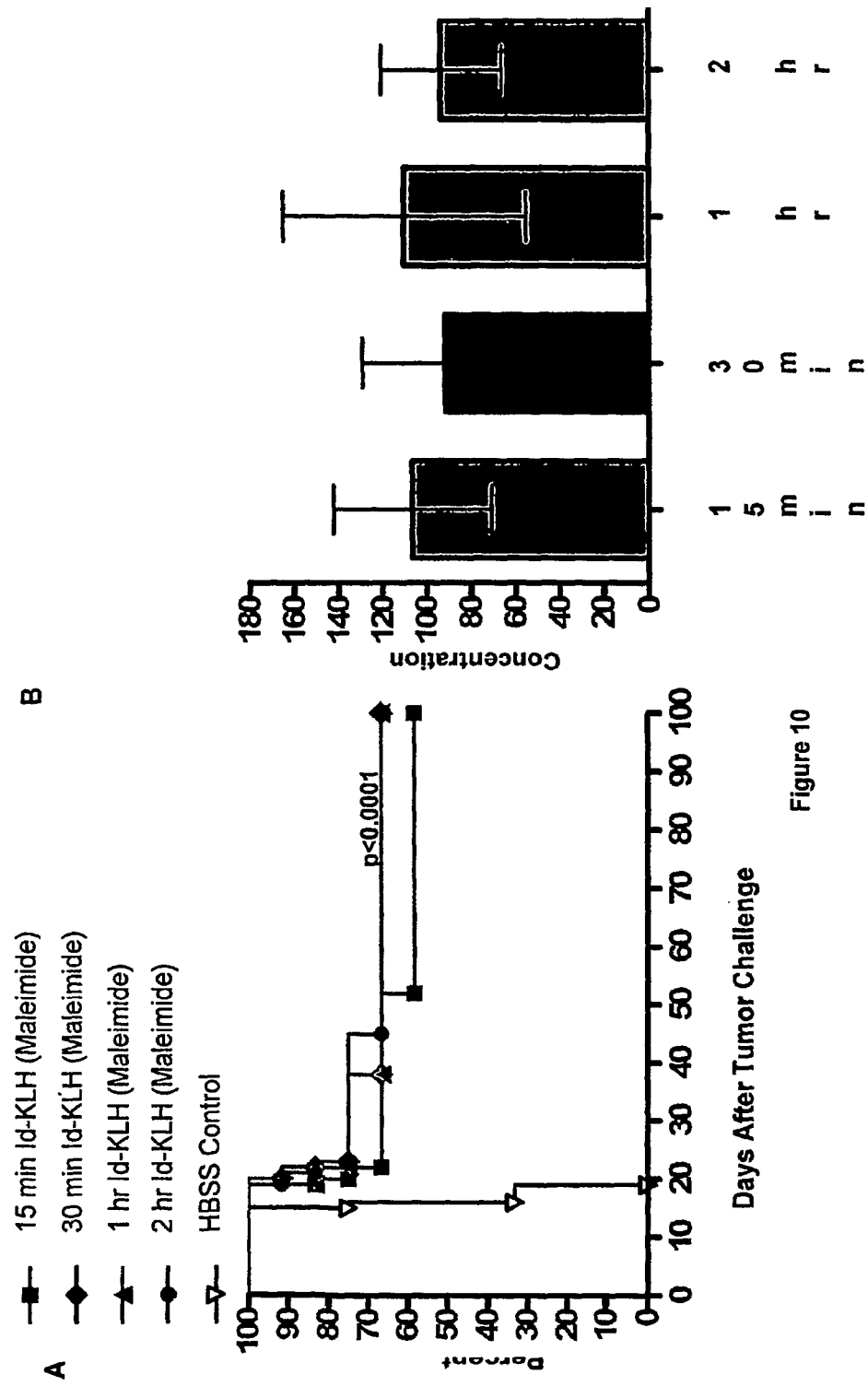

FIG. 10. Id-KLH maleimide conjugations do not show the same time dependency as glutaraldehyde conjugations. Efficacy of maleimide vaccine showed insignificant variation in efficacy against 38C13 challenge when conjugated for varying amounts of time.

Figure 11:
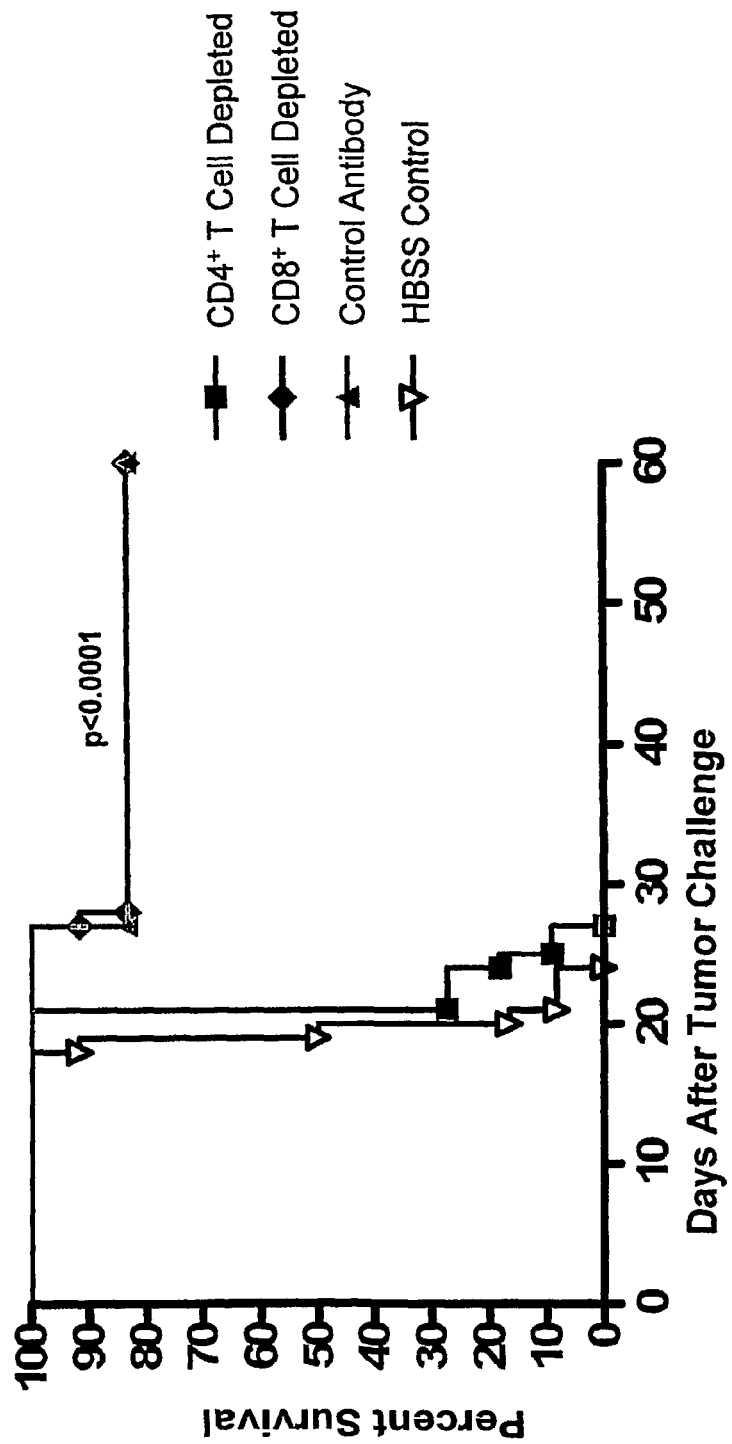

FIG. 11. CD4$^+$ T cells provide protection against 38C13. CD4$^+$ T cell depleted conditions failed to protect against 38C13 tumor challenge when compared with CD8$^+$ T cell depletion.

Figure 12:
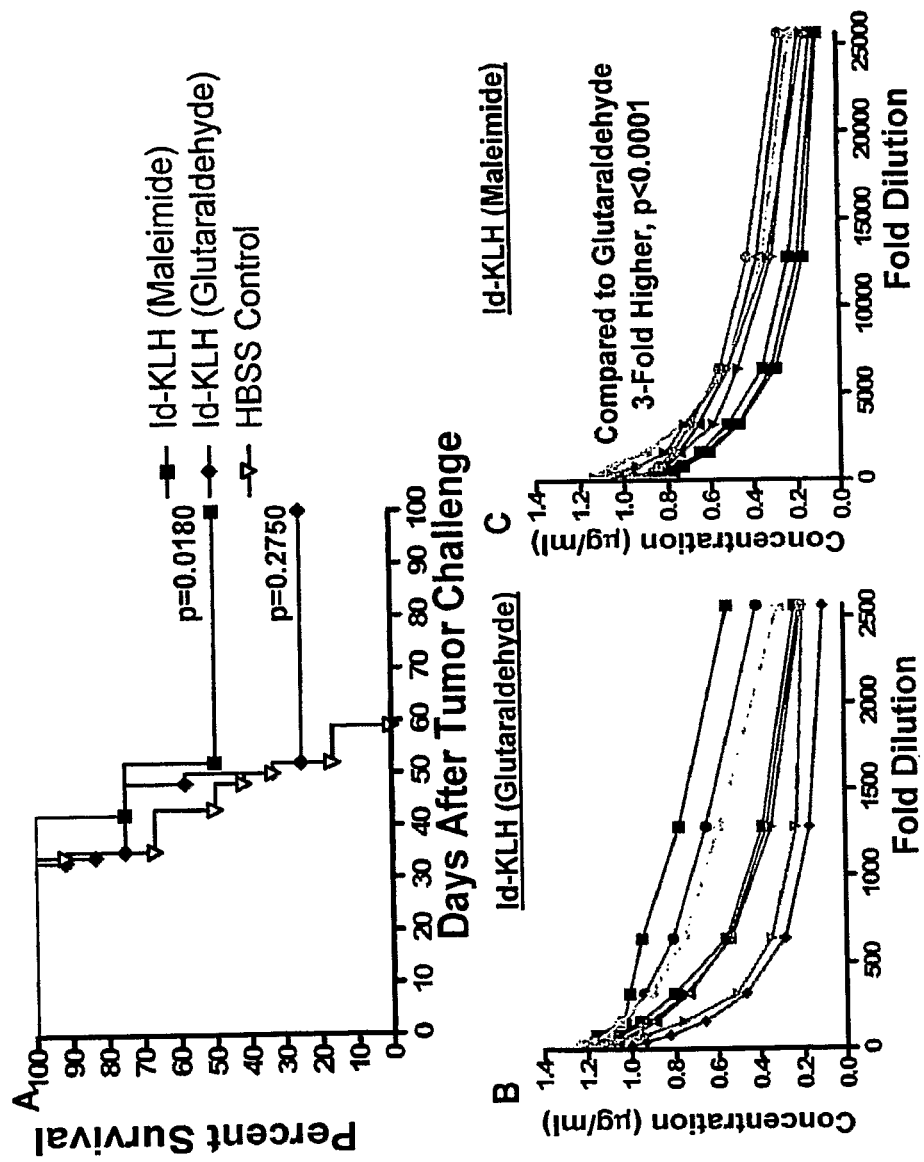
Figure 13:
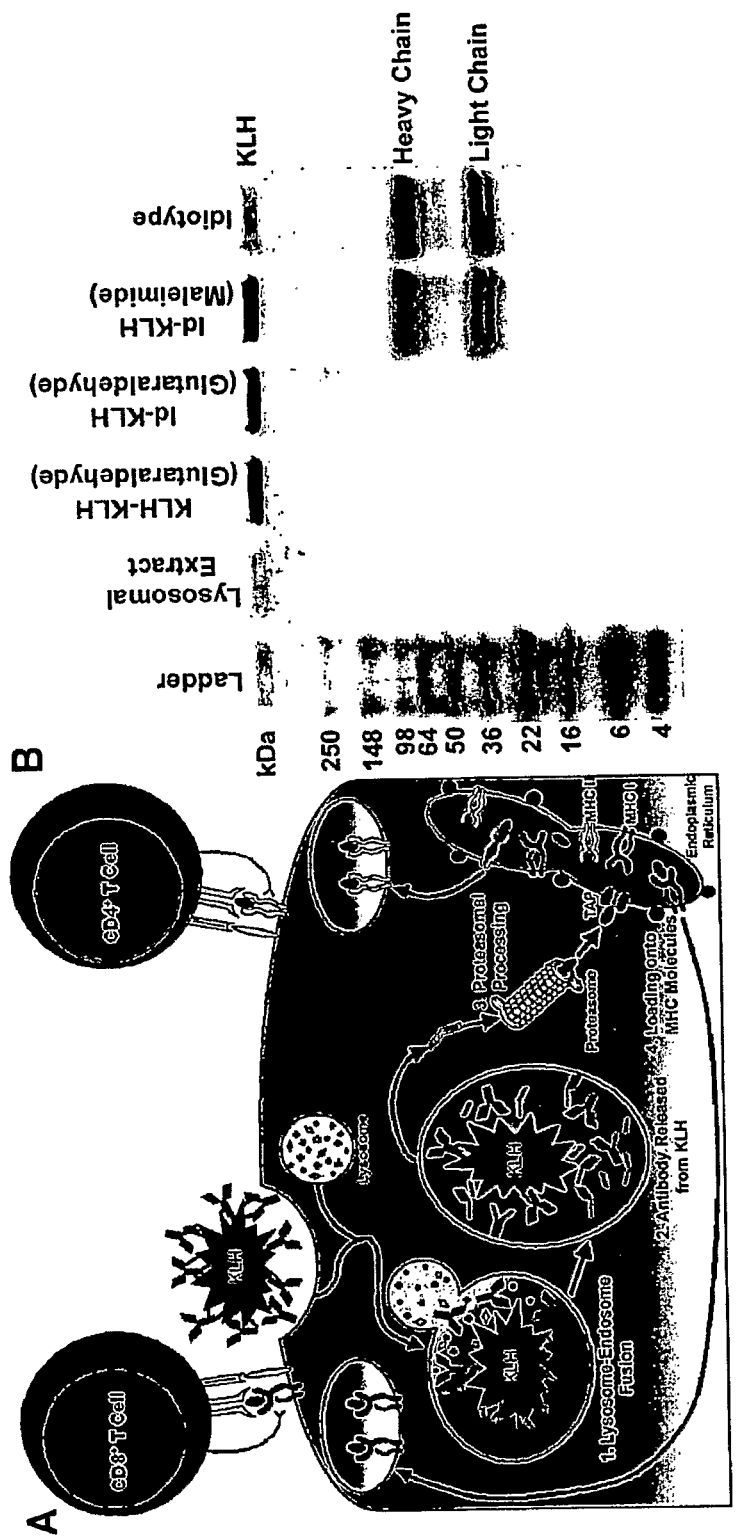

FIG. 12. Id-KLH maleimide conjugates elicit superior anti-tumor immunity and anti-idiotype antibody titers in the BCL-1 B cell lymphoma tumor model. (A) Groups of 12 BALB/c mice were treated with Id-KLH plus GM-CSF vaccines. (B) & (C) Anti-Id antibody levels in the serum of mice vaccinated with maleimide or glutaralhyde Id-KLH were determined 4 days prior to tumor challenge FIG. 13. (A) shows the reversibility of maleimide Id-KLH bonds compared to glutaraldehyde Id-KLH bonds. (B) Id is cleaved from maleimide but not glutaraldehyde Id-KLH conjugates under physical lysosomal processing conditions. KLH conjugated to itself with glutaraldehyde, A20 glutaraldehyde Id-KLH conjugate, A20 maleimide Id-KLH conjugate, or unmodified A20 Id are analyzed be reducing SDS-PAGE and stained with Coomassie brilliant blue.

Figure 14:
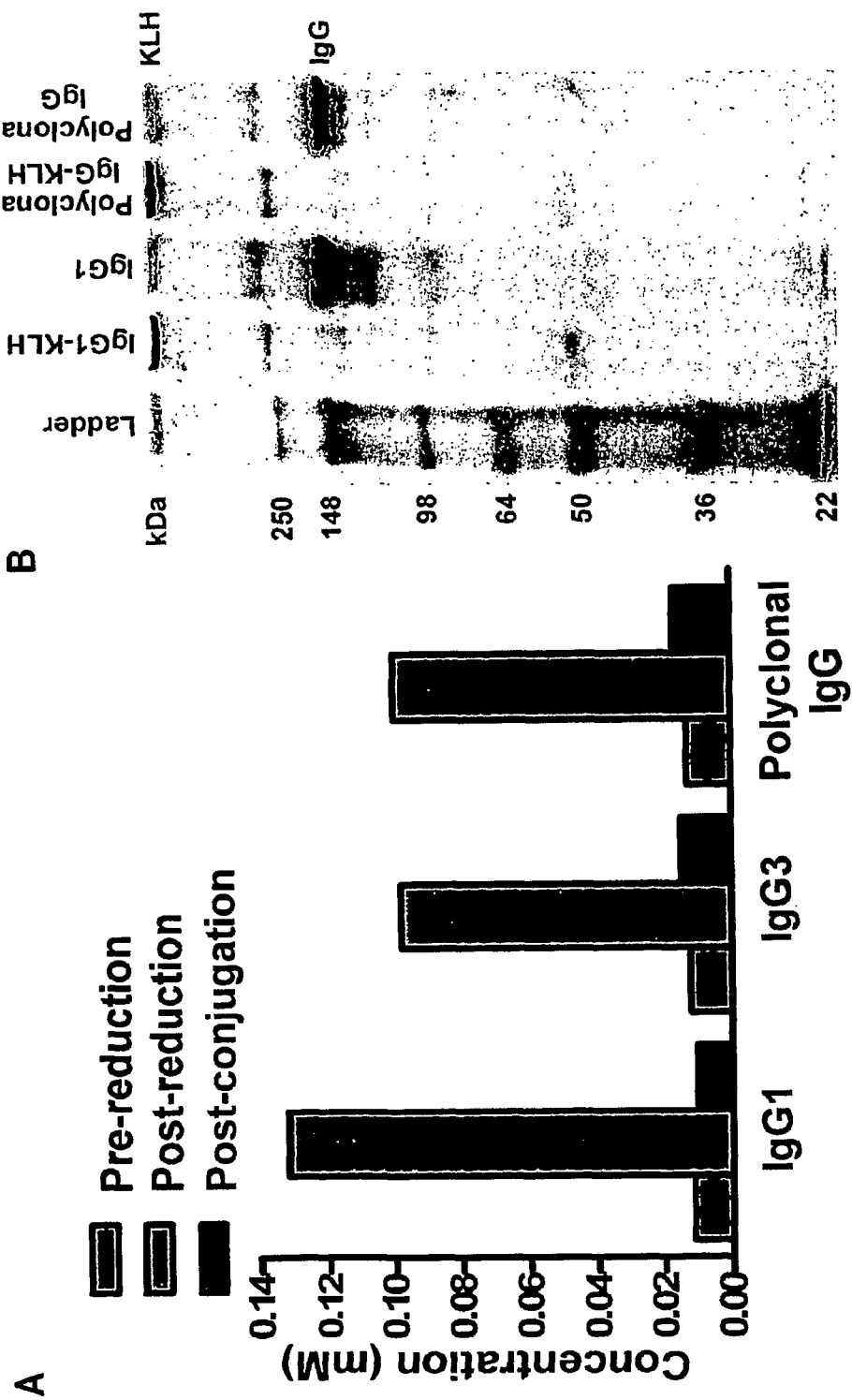

FIG. 14. (A) shows the use of Ellman's reagent in monitoring free sulfhydryl groups during malemide conjugations. Ellman's reagent was used to test human IgG proteins pre-reduction, prost-reduction, and post-conjugation to identify the presence of free sulfhydryl groups at various stages during the conjugation to KLH. (B) shows complete conjugation of human IgGs using maleimide-activated KLH. KLH activated with maleimide (via-sulfo-SMCC) and conjugated to human IgG1 or polyclonal IgG is analyzed by non-reducing SDS-PAGE beside equivalent amount of free IgG1 and polyclonal IgG, and stained with Coomassie brilliant blue.

Figure 15:
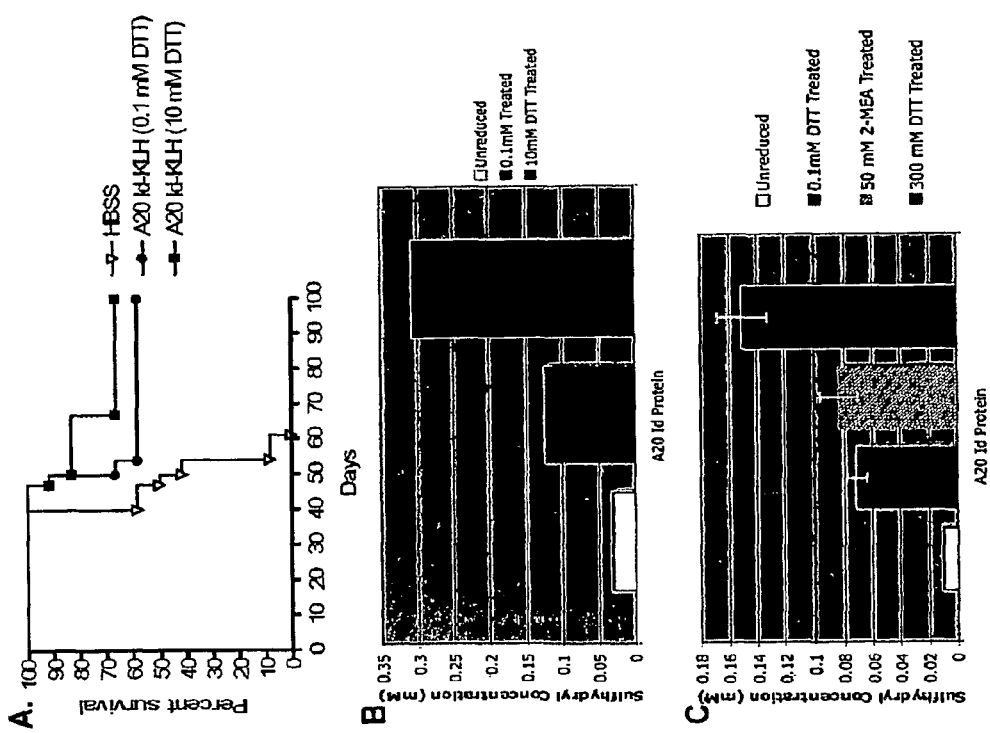

FIG. 15. The effect of DTT reduction on A20 idiotype. Preferred reducing conditions (0.1 mM DTT or 50 mM 2-MEA) result in only partial reduction of the tumor antigen protein.

6. DETAILED DESCRIPTION OF THE INVENTION

In some embodiments, the present invention provides methods of making a vaccine comprising a cleavable linkage. The vaccine may comprise any antigen against which an immune response is desired. For example, in some embodiments, the vaccine is a cancer vaccine. In other embodiments, the vaccine may be directed against a pathogen. In either case, the cancer or pathogenic antigen is partially reduced prior to conjugation with an immunogenic carrier. Then the protein antigen and immunogenic carrier are linked to each other by a bifunctional linker having at least first and second reactive moieties. The first reactive moiety reacts with the protein antigen to form a covalent bond while the second reactive moiety reacts with the immunogenic carrier to form a covalent bond. The covalent bond between the linker and the protein antigen is preferably a thio ether linkage.

"Protein" as used herein can include full length polypeptides and/or peptide fragments thereof, preferably peptides having 50 or more amino acids, 60 or more amino acids, 70 or more amino acids, or 90 or more amino acids. The protein antigen used will depend on the type of vaccine to be manufactured. For example, tumor antigens can be used for cancer vaccines. As used herein, a "tumor antigen" is a proteinaceous molecule made by a tumor cell that is preferentially expressed by the tumor cell as compared to other non-cancerous cells in an organism. Tumor antigens may contain one or more antigenic determinants. In many cases, the tumor antigen, by itself, is incapable of eliciting the significant immune response when used as a cancer vaccine. Accordingly, such tumor antigens are covalently linked to an immunogenic carrier by a linker to enhance the immune response as described more fully herein.

Proteinaceous tumor antigens can be full-length proteins or fragments thereof having 50 or more amino acids, 60 or more amino acids, 70 or more amino acids, or 90 or more amino acids. Such peptides can be derived from a larger protein. While peptides may be used to practice the invention, it is preferred that the full length protein or a major fraction thereof be used so as to minimize the disruption of the three-dimensional structure defining the antigenic determinants of the tumor antigen.

When the tumor antigen is a protein or a peptide of 50 or more amino acids, the tumor antigen is preferably reduced to form at least one sulfhydryl group. This sulfhydryl group reacts with the linker to form the thio ether linkage between the tumor antigen and linker. It is preferred that the reduction conditions be mild so as to minimize the denaturation of the tumor antigen, and to produce a partially-reduced product. "Partially-reduced" as used herein can refer to reduction of cysteine groups of a protein or peptide antigen in which at least one but not all of such groups are modified to form the reduced state, for example, providing at least one sulfhydryl group that can react with the linker, but less than where the protein is completely reduced. Complete reduction would in some cases cause protein chains to unfold and/or separate, destroying conformational epitopes recognizable by B cells. In some embodiments, partial reduction produces at least about 30%, at least about 40%, at least about 50%, at least about 60%, or at least about 70% reduction. "Partial" reduction is used interchangeably herein with "mild," "gentler" and/or "controlled" reduction. In preferred embodiments, only cysteine groups are reduced.

The antigen preferably has at least one sulfhydryl group available to react with the linker. If a disulfide linkage exists within the antigen, that covalent linkage can be reduced to two sulfhydryl groups by use of a mild reducing agent such as dithiothreitol (DTT). In some embodiments, the antigen is partially reduced using a concentration of DTT of less than about 20 mM, less than about 10 mM, less than about 1 mM, less than about 0.1 mM, less than about 0.05 mM, or less than about 0.01 mM. Using 0.1 mM DTT, for example, the reaction can be run or 1 hour at 37 degrees C.

Other reducing agents can also be used. For example, 2-mercaptoethanol, 2-mercaptoethylamine, and/or other mild reducing agents may be used. Dithiothreitol (DTT) and 2-mercaptoethylamine (2-MEA) are preferred reducing reagents. Alternatively, sulfhydryl groups can be introduced artificially into the protein using SATA (N-Succinimidyl-S-acetylthioacetate), SATP (N-Succinimidyl-S-acetylthiopropionate), or Traut's Reagent (2-Iminothiolane.HCl). Preferably, the reducing agents are used under reaction conditions that are controlled to prevent significant denaturation of the antigen.

In preferred embodiments, partial reduction provides a protein antigen that is about 50% reduced. For example, in some embodiments, 0.1 mM DTT provides about 50% reduction. In some embodiments, 50 mM 2-MEA gives about 50% reduction. In other embodiments, the protein antigen may be about less than 70% reduced, less than about 60% reduced or less than about 55% reduced. In other embodiments, the protein antigen may be about more than about 30% reduced, more than about 40% reduced, or more than about 45% reduced.

In some embodiments, additional steps are taken to maintain the desired level of reduction. For example, in some embodiments, the partially-reduced protein antigen is immediately dialyzed into a buffer which maintains its level of reduction. For example, a solution comprising phosphate-buffered saline and EDTA can be used as the buffer. In such cases, the partially-reduced protein antigen can be provided in a solution comprising phosphate-buffered saline and EDTA. In one specific example, 1×PBS pH 7.2 containing 1-100 mM EDTA buffer can be used.

As used herein, "an immunogenic carrier" can be an immunogenic protein or glycoprotein foreign to the tumor host species that is capable of being linked to a weakly immunogenic antigen to form a complex that has superior immunogenic properties. In general, the immunogenic carrier is larger than the antigen. Of the proteinaceous immunogenic carriers, a preferred protein is keyhole limpet hemocyanin (KLH). Other proteinaceous immunogenic carriers include tetanus toxoid, *Klebsiella* ompA, or other immunogenic proteins foreign to the species from which the tumor antigen is derived may be used, e.g., proteins foreign to humans, when a human is a source of tumor antigen.

The antigen and immunogenic carrier are covalently linked via a linker molecule. The linker has at least two active moieties, one of which reacts with the antigen and the other with the immunogenic carrier. In most embodiments, the first and second reactive moieties are different, providing a heterobifunctional linker.

Some embodiments of the invention are based upon the discovery that one or more free sulhydryl groups on a tumor antigen can be used to form a cleavable linkage, e.g., a thio ether linkage, that covalently links the tumor antigen to a immunogenic carrier via the linker. The compounds made according to this protocol surprisingly have enhanced efficacy when used as a tumor vaccine as compared to vaccines wherein the tumor antigen is linked to the carrier using glutaraldehyde. In addition to enhanced survival, the vaccines are also capable of inducing an immune response in animals that are otherwise not responsive to such treatment using glutaraldehyde cross-linked vaccines.

An example of a reactive moiety that reacts with a sulfhydryl group to form a thio ether linkage is maleimide. Maleimides are preferred reactive moieties on the linker that react with free sulfhydryls to form the thio ether bond. The linkage between the linker and the immunogenic carrier can be any linkage although reactive moieties that form an amine linkage are preferred. Examples of reactive moieties that are useful to covalently bind the immunogenic carrier include N-hydroxysuccimide ester. Linkers that can be used in practicing the invention readily can be found in the scientific literature as well as in supply catalogs from Pierce Biotechnology, Rockford, Ill. (WorldWideWeb.piercenet.com). In preferred embodiments, the linker used is group-specific rather than promisicuous, meaning that the linker forms covalent bonds to one or a few types of amino acid residues rather than a large number of different types of residues on the protein antigen. For example, glutaraldehyde can cross-link at cysteine, tyrosine and histidine and would be described as promiscuous, whereas meleimide cross links only with reduced cysteine residues.

Some methods of the invention involve conjugating the linker to the immunogenic carrier and the protein antigen under conditions which permit the formation of a covalent bond between the protein antigen and the first reactive moiety and a covalent bond between the immunogenic carrier and the second reactive moiety, wherein the covalent bond between said linker and the protein antigen is cleavable under lysosomal processing conditions. Without being limited to a specific theory/hypothesis regarding the mechanism of action, use of a partially-reduced protein antigen along with group-specific linkers may facilitate formation of a conjugate that is cleavable under lysosomal processing conditions. For example, as maleimide forms covalent bonds only at reduced cysteine residues, the linkage between the linker and the antigen can be cleaved under lysosomal processing conditions. As used herein, "lysosomal processing conditions" refer to physiological conditions to which an entity being processed by a lysosome is normally subjected. Such conditions are mildly acidic, e.g., pH about 4 to about 5. Cleavage in lysosomes are an important step in eliciting an immune response. Tumor antigen proteins require uptake and proteolytic processing in the lysosomes of antigen presenting cells (APCs) in order to elicit tumor-specific T cell responses (Eisenlohr, L. C. and Rothstein, J. L., *Cancer Treat Res,* 123: 3-36, 2005). Thus, an optimal feature of vaccine conjugates would be to allow cleavage of the protein antigen from its carrier upon uptake by APCs.

In some embodiments, the immunogenic carrier is reacted with the linker and then combined with the partially-reduced protein antigen. In a preferred embodiment, the linker is first covalently attached to the immunogenic carrier. Thereafter, the immunogenic carrier-linker complex is reacted with the protein antigen to form a covalent thio ether linkage. As mentioned, in preferred embodiments, the protein antigen is mildly reduced before reaction with the immunogenic carrier-linker complex. Again, without being limited to a proposed mechanism of action, conjugating to the immunogenic carrier first may further improve specificity of the conjugation reaction with the protein antigen, facilitating cleavability under lysosomal processing conditions.

In some preferred embodiments, the efficacy of the vaccine is independent of the duration of the conjugation step. For example, the conjugation reaction between the protein antigen and linker can be allowed to continue for a range of time periods without significantly affecting the ultimate efficacy of the resulting vaccine. As a specific example, discussed further in the working examples below, Id-KLH maleimide conjugations for 15 mins, 30 mins, 1 hour or 2 hours produce little variation in efficacy of the resulting cancer vaccine, as measured by % survival of C3H mice after tumor challenge.

Another aspect of the present invention relates to compounds made by the above methods. For example, some embodiments of the invention include compounds comprising a proteinaceous tumor antigen, an immunogenic carrier and a linker covalently linking the tumor antigen and the immunogenic carrier by a thio ether linkage. In preferred embodiments, the thio ether linkage is between the tumor antigen and the linker. In some embodiments, the immunogenic carrier is covalently bonded to a linker by other than a thio ether linkage, e.g., amine linkage. The compounds can be used as a vaccine against a cellular proliferative disease that is characterized by the tumor antigen.

As provided in more detail in the working examples, some embodiments of cancer vaccines taught herein can provide superior protection as compared to vaccines known in the art, e.g., vaccines made with a glutaraldehyde linker. For example, some cancer vaccines taught herein can elicit a protective immune response in more than about 50% of a vaccinated population. This is the case seen in each of the mice models A20, 38C13 and BCL-1. Using the same models, however known glutaraldehyde vaccine elicited protective immunity in less than 50% of the vaccinated mice population.

For use as vaccines, in general, compounds described herein can be combined with a pharmaceutically acceptable carrier. In some embodiments, the compound is also combined with an adjuvant such as granulocyte macrophage colony stimulating factor (GM-CSF) and/or other immunologic adjuvant including those containing toll-like receptor ligands (agonists) or cytokines, such as poly I:C and CpG DNA. "Adjuvant" herein is used interchangeably with "immunologic adjuvant" and means a substance which is provided with the antigen or immunogen of choice, e.g., the protein or polypeptide to which an immune response is desired, to enhance the immune response when one attempts to raise an immune response in an animal against the antigen or immunogen of choice, e.g., GM-CSF. One skilled in the art is familiar with appropriate adjuvants to select and use. Adjuvants approved for human use include aluminum salts and MF59 (Singh and O'Hagan, Nature Biotech 17:1075-81, 1999). Other adjuvants are being developed and may be used in conjunction with the present invention. In some embodiments, the composition may contain additional components, such as stabilizers, excipients, and the like, as described in more Compounds described herein can be used in cancer vaccines directed to a number of different cellular proliferative diseases including B-cell proliferative diseases (non-Hodgkin's B cell lymphoma, follicular lymphoma), T-cell proliferative diseases, myeloid cancers, and solid tumors derived from epithelial, mesenchymal, neuronal, or germ cell tissues. When administered to a cancer patient having a B-cell or T-cell proliferative disease, the vaccine generates an immune response which is directed to at least one epitope of the tumor antigen from a proliferative B- or T-cell. Vaccination can result in humoral and/or cell mediated response that is directed against an antigenic epitope of the tumor cell from which the tumor antigen is derived.

B-cell proliferative diseases include B-cell lymphomas, leukemia, multiple myeloma and light chain amyloidosis. Idiotypic antibodies are associated with B-cell proliferative diseases. An idiotypic antibody contains one or more antigenic determinants that are specific for the clonal B-cells causing the B-cell proliferative disease.

T-cell proliferative diseases include T-cell lymphomas and leukemias. In the case of T-cell proliferative diseases, a T-cell antigen receptor (TCR) has one or more antigenic determinants that are specific for the clonal T-cells causing the T-cell proliferative disease In some embodiments, the antigenic protein is an idiotypic antibody or a peptide derived from an idiotypic antibody containing one or more tumor specific antigenic determinants. The idiotypic antibody is generally associated with a B-cell proliferative diseases such as lymphoma, leukemia, multiple myeloma or light chain amyloidosis.

In another embodiment, the antigenic protein is a TCR or a peptide derived from a TCR containing one or more tumor specific antigenic determinants. In these embodiments, the TCR is associated with a T-cell proliferative disease such as T-cell lymphoma or leukemia.

The cancer vaccines of some embodiments of the present invention can comprise at least one epitope of at least one tumor antigen. Most preferably, polytope vaccines are provided comprising a plurality of epitopes from one or more tumor antigens. The tumor antigens finding use in the subject compositions and methods may be inherently immunogenic, or non-immunogenic, or slightly immunogenic. Exemplary antigens include, but are not limited to, synthetic, recombinant, foreign, or homologous antigens, and antigenic materials may include but are not limited to proteins, peptides, polypeptides, lipids, glycolipids, carbohydrates and DNA.

In some embodiment, the tumor antigen is a protein or a peptide having 50 or more amino acids containing one or more antigenic determinants. In particularly preferred embodiments, one or more of these antigenic determinants specifically define the cellular source of the proliferative disease. Such tumor antigens may be derived from proteinaceous tumor antigens such as a tumor-specific idiotypic protein. Alternatively, when the tumor antigen is a peptide having 50 or more amino acids, the peptide may be derived from these and other antigenic tumor proteins.

Tumor antigens suitable for use in the subject invention include both mutated and non-mutated molecules which may be indicative of single tumor type, shared among several types of tumors, and/or exclusively expressed or overexpressed in tumor cells in comparison with normal cells. In addition to proteins and glycoproteins, tumor-specific patterns of expression of carbohydrates, gangliosides, glycolipids and mucins have also been documented. Exemplary tumor antigens for use in the subject cancer vaccines include protein products of oncogenes, tumor suppressor genes and other genes with mutations or rearrangements unique to tumor cells, reactivated embryonic gene products, oncofetal antigens, tissue-specific (but not tumor-specific) differentiation antigens, growth factor receptors, cell surface carbohydrate residues, foreign viral proteins and a number of other self proteins.

Specific embodiments of tumor antigens include, e.g., mutated antigens such as the protein products of the Ras p21 protooncogenes, tumor suppressor p53 and HER-2/neu and BCR-abl oncogenes, as well as CDK4, MUM1, Caspase 8, and Beta catenin; overexpressed antigens such as galectin 4, galectin 9, carbonic anhydrase, Aldolase A, PRAME, Her2/neu, ErbB-2 and KSA, oncofetal antigens such as alpha fetoprotein (AFP), human chorionic gonadotropin (hCG); self antigens such as carcinoembryonic antigen (CEA) and melanocyte differentiation antigens such as Mart 1/Melan A, gp100, gp75, Tyrosinase, TRP1 and TRP2; prostate associated antigens such as PSA, PAP, PSMA, PSM-P1 and PSM-P2; reactivated embryonic gene products such as MAGE 1, MAGE 3, MAGE 4, GAGE 1, GAGE 2, BAGE, RAGE, and other cancer testis antigens such as NY-ESO1, SSX2 and SCP1; mucins such as Muc-1 and Muc-2; gangliosides such as GM2, GD2 and GD3, neutral glycolipids and glycoproteins such as Lewis (y) and globo-H; and glycoproteins such as Tn, Thompson-Freidenreich antigen (TF) and sTn. Also included as tumor antigens herein are whole cell and tumor cell lysates as well as immunogenic portions thereof, as well as immunoglobulin idiotypes expressed on monoclonal proliferations of B lymphocytes for use against B cell lymphomas.

Particularly preferred example of protein tumor antigens that could be used as carrier-protein conjugate vaccines include tumor-specific idiotypic immunoglobulins, tumor-specific T-cell antigen receptors (TCRs), HER-2/neu, bcr/abl, p21ras, mutated p53, MAGE-1, MAGE-3, BAGE, GAGE, RAGE, MART-1Melan A, gp100, prostate-specific membrane antigen, prostate specific antigen, prostatic alkaline phosphatase, carcinoembryonic antigen, MUC-1, human papilloma virus E6 and E7, Epstein-Bar virus EBNA-1 and LMP-1, tyrosine, telomerase reverse transcriptase (hTERT) and survivin. Such antigens can find use in vaccines for treating patients having cancers expressing one or more of the corresponding antigens. In some embodiments, the tumor antigen is other than a tumor-specific idiotypic immunoglobulin.

Tumor antigens and their respective tumor cell targets include, e.g., cytokeratins, particularly cytokeratin 8, 18 and 19, as antigens for carcinoma. Epithelial membrane antigen (EMA), human embryonic antigen (HEA-125), human milk fat globules, MBr1, MBr8, Ber-EP4, 17-1A, C26 and T16 are also known carcinoma antigens. Desmin and muscle-specific actin are antigens of myogenic sarcomas. Placental alkaline phosphatase, beta-human chorionic gonadotropin, and alpha-fetoprotein are antigens of trophoblastic and germ cell tumors. Prostate specific antigen is an antigen of prostatic carcinomas, carcinoembryonic antigen of colon adenocarcinomas. HMB-45 is an antigen of melanomas. In cervical cancer, useful antigens could be encoded by human papilloma virus. Chromagranin-A and synaptophysin are antigens of neuroendocrine and neuroectodermal tumors.

Tumor antigens can be prepared by methods well known in the art. For example, these antigens can be prepared from cancer cells either by preparing crude extracts of cancer cells (e.g., as described in Cohen et al., Cancer Res., 54:1055 (1994)), by partially purifying the antigens, by recombinant technology, or by de novo synthesis of known antigens. The antigen may also be in the form of a nucleic acid encoding an antigenic peptide in a form suitable for expression in a subject and presentation to the immune system of the immunized subject. Further, the antigen may be a complete antigen, or it may be a fragment of a complete antigen comprising at least one epitope.

Antigens derived from pathogens known to predispose to certain cancers may also be advantageously included in the cancer vaccines of the present invention. It is estimated that close to 16% of the worldwide incidence of cancer can be attributed to infectious pathogens; and a number of common malignancies are characterized by the expression of specific viral gene products. Thus, the inclusion of one or more antigens from pathogens implicated in causing cancer may help broaden the host immune response and enhance the prophylactic or therapeutic effect of the cancer vaccine. Pathogens of particular interest for use in the cancer vaccines provided herein include the hepatitis B virus (hepatocellular carcinoma), hepatitis C virus (heptomas), Epstein Barr virus (EBV) (Burkitt lymphoma, nasopharynx cancer, PTLD in immunosuppressed individuals), HTLV1 (adult T cell leukemia), oncogenic human papilloma viruses types 16, 18, 33, 45 (adult cervical cancer), and the bacterium *Helicobacter pylori* (B cell gastric lymphoma). Other medically relevant microorganisms that may serve as antigens in mammals and more particularly humans are described extensively in the literature, e.g., C. G. A Thomas, Medical Microbiology, Bailliere Tindall, Great Britain 1983, the entire contents of which is hereby incorporated by reference.

Other embodiments can find use in the design of antigen-carrier conjugate vaccines for other purposes, e.g., for pathogenic diseases. Such diseases may include, e.g., diseases caused by infectious disease agents. In such cases, vaccine efficacy can be improved by improving the cleavability of the antigen from its carrier, in a similar way as has been demonstrated with respect to cancer vaccines herein.

The pathogen vaccines of some embodiments of the instant invention can comprise at least one epitope of at least one antigen derived from a pathogen. Pathogens which may be targeted by the subject vaccines include, but are not limited to infectious virus, infectious bacteria, infectious parasites and infectious fungi. Most preferably, polytope vaccines are provided comprising a plurality of epitopes from one or more such antigens. The microbial antigens used may be inherently immunogenic, or non-immunogenic, or slightly immunogenic. Exemplary antigens include, but are not limited to, synthetic, recombinant, foreign, or homologous antigens, and antigenic materials may include but are not limited to proteins, peptides, polypeptides, lipids, glycolipids, carbohydrates and DNA.

Exemplary viral pathogens include, but are not limited to, infectious virus that infect mammals, and more particularly humans. Examples of infectious virus include, but are not limited to: Retroviridae (e.g. human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e,g. vesicular stomatitis viruses, rabies viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Also, gram negative and gram positive bacteria may be targeted by the subject compositions and methods in vertebrate animals. Such gram positive bacteria include, but are not limited to *Pasteurella* species, *Staphylococci* species, and *Streptococcus* species. Gram negative bacteria include, but are not limited to, *Escherichia coli*, *Pseudomonas* species, and *Salmonella* species. Specific examples of infectious bacteria include but are not limited to: *Helicobacter pyloris*, *Borelia burgdorferi, Legionella pneumophilia, Mycobacteria* sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), Streptococcusfaecalis, *Streptococcus bovis, Streptococcus (anaerobic* sps.), *Streptococcus pneumoniae,* pathogenic *Campylobacter* sp., *Enterococcus* sp., *Haemophilus infuenzae, Bacillus antracis, corynebacterium diphtheriae, corynebacterium* sp., *Erysipelothrix rhusiopathiae, Clostridium perfringers, Clostridium tetani, Enterobacter aerogenes, Kiebsiella pneumoniae, Pasturella multocida, Bacteroides* sp., *Fusobacterium nucleatum, Streptobacillus moniliformis, Treponema pallidium, Treponema pertenue, Leptospira, Rickettsia,* and *Actinomyces israelli*.

Polypeptides of bacterial pathogens which may find use as sources of microbial antigens in the subject compositions include but are not limited to an iron-regulated outer membrane protein, ("IROMP"), an outer membrane protein ("OMP"), and an A-protein of *Aeromonis salmonicida* which causes furunculosis, p57 protein of *Renibacterium salmoninarum* which causes bacterial kidney disease ("BKD"), major surface associated antigen ("msa"), a surface expressed cytotoxin ("mpr"), a surface expressed hemolysin ("ish"), and a flagellar antigen of Yersiniosis; an extracellular protein ("ECP"), an iron-regulated outer membrane protein ("IROMP"), and a structural protein of Pasteurellosis; an OMP and a flagellar protein of *Vibrosis anguillarum* and *V. ordalii*; a flagellar protein, an OMP protein, aroA, and purA of *Edwardsiellosis ictaluri* and *E. tarda*; and surface antigen of Ichthyophthirius; and a structural and regulatory protein of *Cytophaga columnari*; and a structural and regulatory protein of *Rickettsia*. Such antigens can be isolated or prepared recombinantly or by any other means known in the art.

Examples of pathogens further include, but are not limited to, infectious fungi that infect mammals, and more particularly humans. Examples of infectious fungi include, but are not limited to: *Cryptococcus neoformans, Histoplasma capsulatum, Coccidioides immitis, Blastomyces dermatitidis, Chiamydia trachomatis, Candida albicans*. Examples of infectious parasites include *Plasmodium* such as *Plasmodium falciparum, Plasmodium malariae, Plasmodium ovale,* and *Plasmodium vivax*. Other infectious organisms (i.e. protists) include *Toxoplasma gondii*. Polypeptides of a parasitic pathogen include but are not limited to the surface antigens of Ichthyophthirius.

Other medically relevant microorganisms that serve as antigens in mammals and more particularly humans are described extensively in the literature, e.g., see C. G. A Thomas, Medical Microbiology, Bailliere Tindall, Great Britain 1983, the entire contents of which is hereby incorporated by reference. In addition to the treatment of infectious human diseases and human pathogens, the compositions and methods of the present invention are useful for treating infections of nonhuman mammals. Many vaccines for the treatment of non-human mammals are disclosed in Bennett, K. Compendium of Veterinary Products, 3rd ed. North American Compendiums, Inc., 1995; see also WO 02/069369, the disclosure of which is expressly incorporated by reference herein.

Exemplary non-human pathogens include, but are not limited to, mouse mammary tumor virus ("MMTV"), Rous sarcoma virus ("RSV"), avian leukemia virus ("ALV"), avian myeloblastosis virus ("AMV"), murine leukemia virus ("MLV"), feline leukemia virus ("FeLV"), murine sarcoma virus ("MSV"), gibbon ape leukemia virus ("GALV"), spleen necrosis virus ("SNV"), reticuloendotheliosis virus ("RV"), simian sarcoma virus ("SSV"), Mason-Pfizer monkey virus ("MPMV"), simian retrovirus type 1 ("SRV-1"), lentiviruses such as HIV-1, HIV-2, SIV, Visna virus, feline immunodeficiency virus ("FIV"), and equine infectious anemia virus ("EIAV"), T-cell leukemia viruses such as HTLV-1, HTLV-II, simian T-cell leukemia virus ("STLV"), and bovine leukemia virus ("BLV"), and foamy viruses such as human foamy virus ("HFV"), simian foamy virus ("SFV") and bovine foamy virus ("BFV").

Microbial antigens can be prepared by methods well known in the art. For example, these antigens can be prepared directly from viral and bacterial cells either by preparing crude extracts, by partially purifying the antigens, or alternatively by recombinant technology or by de novo synthesis of known antigens. The antigen may also be in the form of a nucleic acid encoding an antigenic peptide in a form suitable for expression in a subject and presentation to the immune system of the immunized subject. Further, the antigen may be a complete antigen, or it may be a fragment of a complete antigen comprising at least one epitope.

Another aspect of the present invention relates to methods of treatment. Some embodiments provide a method of treatment comprising administering in a therapeutic amount one or more of the vaccine compositions described herein to patient in need thereof. In preferred embodiments, "treatment", "treat", "treating" as used herein refers to a prophylactic treatment which increases the resistance of a subject to susceptibility to a cancer and/or to infection with a pathogen; and/or treatment after the subject has developed a cancer and/or become infected, treatment refers to increased ability to fight the cancer and/or infection, e.g., to reduce or eliminate the cancer/infection or prevent it from becoming worse. The formulations of some embodiments of the invention may be administered in pharmaceutically acceptable solutions, which may routinely contain pharmaceutically acceptable concentrations of salt, buffering agents, preservatives, compatible carriers, adjuvants, and optionally other therapeutic ingredients.

Vaccine compositions of the instant invention can be administered in a therapeutic amount. By "therapeutic amount" is meant an amount where the active ingredients are administered in an amount effective to achieve its intended purpose. More specifically, therapeutic amount can mean an amount of the compound effective to prevent, alleviate or ameliorate symptoms of disease or prolong survival of the subject being treated. Determination of a therapeutically effective amount is well within the capability of those skilled in the art, in light of the detailed disclosure provided herein. For example, the results obtained using 2 mouse models (A20, 38C13 and BLC-1), traditionally used in evaluating cancer vaccines, provides data that can be translated by those of skill in the art to determine appropriate therapeutic amounts for use in human subjects.

For use in therapy, an effective amount of the vaccines of the present invention can be administered to a subject by any mode allowing uptake by the appropriate target cells. "Administering" the vaccine compositions may be accomplished by any means known to the skilled artisan. Preferred routes of administration include but are not limited to parenteral injection (subcutaneous, intradermal, intravenous, parenteral, intraperitoneal, intrathecal, etc.) as well as mucosal, intranasal, intratracheal, inhalation, and intrarectal, intravaginal; or oral, transdermal (e.g., via a patch). An injection may be in a bolus or a continuous infusion.

For example, the vaccine compositions of the present invention can be administered by subcutaneous, intramuscular or intradermal injection, or other parenteral means, or by biolistic "gene-gun" application to the epidermis. The compositions of the present invention may also be administered, for example, by inhalation, topically, intravenously, orally, implantation, rectally, or vaginally. Suitable liquid or solid pharmaceutical preparation forms are, for example, aqueous or saline solutions for injection or inhalation, encochleated, coated onto microscopic gold particles, and nebulized. For a brief review of present methods for drug delivery, see Langer, Science 249:1527-1533, 1990, which is incorporated herein by reference.

The pharmaceutical compositions are preferably prepared and administered in dose units. Liquid dose units are vials or ampoules for injection or other parenteral administration. Solid dose units are tablets, capsules and suppositories. For treatment of a patient, depending on activity of the compound, manner of administration, purpose of the immunization (i.e., prophylactic or therapeutic), nature and severity of the disorder, age and body weight of the patient, different doses may be necessary. The administration of a given dose can be carried out both by single administration in the form of an individual dose unit or else several smaller dose units. Multiple administration of doses at specific intervals of weeks or months apart is usual for boosting the antigen-specific responses.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

In preferred embodiments, the compositions of the present invention contain an effective amount of a combination of adjuvants and antigens optionally included in a pharmaceutically-acceptable carrier. "Pharmaceutically-acceptable carrier" as used herein refers to one or more compatible solid or liquid filler, dilutants or encapsulating substances which are suitable for administration to a human or other mammal. "Carrier" as used herein with respect to pharmaceutically-acceptable carriers refers to an organic or inorganic ingredient, natural or synthetic, with which the active ingredient is combined to facilitate the application.

Compositions suitable for parenteral administration conveniently comprise sterile aqueous preparations, which can be isotonic with the blood of the recipient. Among the acceptable vehicles and solvents are water, Ringer's solution, phosphate buffered saline and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for subcutaneous, intramuscular, intraperitoneal, intravenous, etc. administrations may be found in Remington's Pharmaceutical Sciences, Mack Publishing Company, Easton, Pa.

The adjuvants or antigens useful in the invention may be delivered in mixtures of more than two adjuvants or antigens. A mixture may consist of several adjuvants in addition to the vaccine formulations described herein.

A variety of administration routes are available. The particular mode selected will depend, of course, upon the particular adjuvants or antigen selected, the age and general health status of the subject, the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration are discussed above.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to; (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

7. EXAMPLES

The following is directed to B-cell lymphoma models and the production of idiotypic antibody conjugate with KLH via a thioether linkage. The approaches used in this embodiment are generally applicable to other proliferative diseases and more generally to other cleavable conjugates useful in vaccines.

The approach to Id-KLH vaccination using a sulfhydryl-based conjugation chemistry (maleimide) to link tumor antigen to the KLH carrier protein was tested. Several well-characterized murine lymphoma models demonstrated a surprising level of efficacy in comparison with the traditional glutaraldehyde methodologies, which are currently viewed as industry standards after over 20 years of investigational usage. Methods described herein allowed one Id vaccine (A20 lymphoma), previously believed to be unresponsive to Id-KLH vaccination (Biragyn, A. and Kwak, L. W. Models for Lymphoma. In: A. M. K. J. E. Coligan, D. H. Margulies, E. M. Shevach, W. Strober, and R. Coico, editors. (ed.), *Current Protocols in Immunology*, pp. 20.26.21-20.26.30. Hoboken, N.J.: John Wiley & Sons, Inc., 2001) to have striking efficacy at eradicating established tumors. Moreover, the prototypical 38C13 model also showed superior anti-tumor effects with the maleimide Id-KLH vaccine described herein. Results in a third model (BCL-1) George et al, *J Immunol*, 141: 2168-2174, 1988) indicate again the superiority of maleimide Id-KLH over glutaraldehyde Id-KLH.

Materials and Methods

Animals.

BALB/c and C3H mice (6-10 wks of age) were used for in vivo experiments. Mice were housed in the Radiation Oncology Barrier Facility, a defined pathogen colony at UCLA (Los Angeles, Calif.), and experiments conducted according to UCLA animal care guidelines.

Cell Lines.

The spontaneously arising $IgG_{2a}/\kappa$ expressing A20 BALB/c B cell lymphoma line was obtained from the American Type Culture Collection (ATCC) (Rockville, Md.) (Kim, K. J., et al., *J Immunol*, 122: 549-554, 1979). 38C13 (a gift from Dr. Ronald Levy, Sanford, Calif.) is a carcinogen-induced murine B cell lymphoma in C3H that expresses a surface IgM/κ (Bergman, Y. and Haimovich, J., *Eur J Immunol*, 7: 413-417, 1977). BCL-1 (a gift from Dr. Samuel Strober, Stanford, Calif.) is another spontaneously arising BALB/c B cell lymphoma that expresses a surface IgM/λ (Warnke, R. A., et al., *J Immunol*, 123: 1181-1188, 1979). Tumor cells were cultured in RPMI 1640 media (Gibco Life Technologies, Inc., Rockville, Md.) supplemented with 10% heat-inactivated FCS (Omega Scientific, Tarzana, Calif.), 100 Units/ml penicillin/streptomycin (Gibco Life Technologies, Inc., Rockville, Md.), 2 mM L-glutamine (Gibco), and 50 µM β-mercaptoethanol (Gibco). Tumor cells were grown at 37° C. in 5% $CO_2$.

Antibodies.

38C13 idiotype (Id)(38C13-A1.2, IgM/□) and BCL-1 Id (6A5.1, IgM/□) proteins were isolated from tumor-myeloma hybridomas as previously described (Kaminski, M. S., et al., *J Immunol*, 138: 1289-1296, 1987; Timmerman, J. M., et al., *Blood*, 97: 1370-1377., 2001). The Id proteins were affinity purified by mannose binding protein columns (Pierce) to greater than 95% purity based on sodium dodecyl sulfate-polyacrylamide gel electrophoresis (SDS-PAGE) and quantitated via ELISA. Anti-idiotype antibodies S1C5 (ant-38C13 Id, mouse $IgG_{2a}$), B1 (BCL-1 anti-Id, mouse $IgG_1$) (a gift from Dr. Kris Thielemans, Brussels, Belgium), and 1G6 (A20 anti-Id, $IgG_1$) (a gift from Dr. Ronald Levy, Stanford, Calif.) were purified from culture supernatants (Maloney, D. G., et al., *Hybridoma*, 4: 191-209, 1985; Brissinck, J., et al., *J Immunol*, 147: 4019-4026, 1991) using protein A-Fast Flow columns (Amersham, Piscataway, N.J.) and quantitated via ELISA. The $CD8^+$ T cell-depleting antibody HB129 (mouse $IgG_{2a}$) (ATCC) and the NK-depleting antibody TMβ1 (anti-IL-2Rβ, rat $IgG_{2b}$) (a gift from Dr. Toshiyuki Tanaka) were generated from ascites. The anti-CD4 (GK1.5, rat $IgG_{2b}$) and anti-CD8α (53.6.72, rat $IgG_1$) T cell-depleting antibodies were purchased from BioExpress (West Lebanon, N.H.). Control rat IgG and mouse $IgG_{2a}$(UPC-10) were purchased from Sigma-Aldrich (St. Louis, Mo.).

Generation of A20 Idiotype-Producing Hybridoma.

A20 tumor cells sensitive to hypoxanthine, aminopterin, and thymidine (HAT) were derived by growing the cells for six weeks in progressively higher concentrations of 5-bromodeoxyuridine (BrdU) (Sigma-Aldrich, St. Louis, Mo.) and fused to a myeloma cell line to create an A20 rescue hybrid, as described previously (Maloney, D. G., et al., *Hybridoma*, 4: 191-209, 1985). Briefly, the BrdU-resistant A20 line was fused to SP2/0, a non-secreting, 8-azaguanine-resistant, and HAT sensitive myeloma line (CRL-8287, ATCC) with 45% pre-warmed polyethylene glycol (Sigma-Aldrich) at a ratio of 2:1 (A20:SP2/0) for 2 minutes at 37° C., then grown in RPMI 1640 complete media with 25 mM HEPES and 1×HAT. HAT-resistant cells cultures secreting IgG2a were cloned by limiting dilution, and the highest producing clone (3D6) was selected. The Ig variable regions of 3D6 were amplified, sequenced, and found to have complete identity to the parental wild-type A20 Ig sequences.

To purify the secreted A20 IgG2a, subline 3D6.3 was adapted to serum free growth in PFHM II media (Gibco Life Technologies, Inc., Rockville, Md.) supplemented with 10 Units/m) penicillin/streptomycin, 2 mM L-glutamine, and 50 µM β-mercaptoethanol. IgG2a was purified using protein A-Fast Flow columns (Amersham), elution with 3 M potassium thiocyanate, concentrated in YM-30 spin concentrators (Millipore, Bedford, Mass.), and dialyzed against 1×PBS. ELISA and SDS-PAGE were performed to determine quantity and purity of Id protein.

Detection of Free Sulfhydryl Groups with Ellman's Reagent.

A set of cysteine standards was prepared using cysteine hydrochloride monohydrate in reaction buffer (0.1 M sodium phosphate, pH 8.0, containing 1 mM EDTA) (Pierce) ranging in concentration from 1.5 to 0 mM. 50 µl of Ellman's reagent solution (4 mg/ml Ellman's reagent in reaction buffer) (Pierce) were added to 2.5 ml of reaction buffer. 250 µl of each standard and various dilutions of the non-treated, reduced, or conjugated immunoglobulins (0.1-1.0 mM concentration is ideal for standard curve working range) were added to tubes containing Ellman's reagent. Tubes were mixed and incubated at room temperature for 15 minutes. Absorbance was measured at 412 nm using a SPECTRAmax Plus 384 microplate reader (Molecular Devices, Menlo Park, Calif.), and values for each protein determined from the standard curve to quantify free sulfhydryl groups.

Ellman's reagent is used to verify the reduction of sulfhydryl groups in the tumor antigen prior to conjugation with maleimide-activated KLH, and to assure complete reaction of these groups following conjugation. The following provides a specific example of the details of protocol that can be used to detect free sulfhydryl groups:
1. Prepare a set of cysteine standards using cysteine hydrochloride monohydrate in reaction buffer (0.1 M sodium phosphate, pH 8.0, containing 1 mM EDTA) (Pierce, Rockford, Ill.) ranging in concentration from 1.5 to 0 mM.
2. Add 50 μl of Ellman's reagent solution (4 mg/ml Ellman's reagent in reaction buffer) (Pierce, Rockford, Ill.) to 2.5 ml of reaction buffer,
3. Place 250 μl of each standard and various dilutions of the pre-reduction, post-reduction, or post-conjugated idiotype/tumor antigen (0.1-1.0 mM concentration is ideal for standard curve working range) into tubes containing Ellman's reagent.
4. Mix tubes and incubate at room temperature for 15 minutes.
5. Measure absorbance at 412 nm using a SPECTRAmax Plus 384 microplate reader (Molecular Devices, Menlo Park, Calif.) to identify the presence of free sulfhydryls.

Following conjugation, the amount of sulfhydryls detected should return to the baseline, pre-reduction level.

Idiotype-KLH Conjugations.

FIG. 1A illustrates the conjugation chemistries for the two cross-linking agents used in this study. Glutaraldehyde conjugations were generally performed for 15-30 minutes on a rocker at room temperature using 1:1 (w:w) mixtures of Id:KLH in a final concentration of 0.1% glutaraldehyde (Sigma-Aldrich) as previously-described (Campbell, M. J., et al., *J Immunol,* 139: 2825-2833, 1987). Conjugations were carried out until a thready, insoluble precipitate began to form, and terminated by initiating dialysis against 1×PBS at 4° C. For glutaraldehyde conjugation timecourse studies, Id proteins were conjugated to KLH for 0, 2, 15, 30, 60, or 120 minutes before initiation of dialysis. FIG. 1B graphically depicts predicted interactons between KLH and idiotype proteins via glutaraldehyde and maleimide methods.

For maleimide conjugations, Id proteins were first reduced in a final concentration of 0.1 mM dithiothreitol (Sigma-Aldrich) for 1 hour at 37° C. and dialyzed into 1×PBS containing 0.1 M EDTA buffer to prevent re-oxidation of sulfhydryls. Under these conditions, the resulting reduction was partial, reaching approximately 50% of maximal reduction achieved using 300 mM DTT and boiling for 10 minutes. Reduced Id proteins were then conjugated to maleimide-activated KLH (Pierce) at a 1:1 ratio of Id to KLH (w:w) on a rocker platform for 2 hours at room temperature, followed by dialysis against 1×PBS 4° C. Maleimide conjugations were quality controlled with Ellman's reagent (Pierce) to determine the free sulfhydryl content of the Id protein before and after conjugation, to ensure availability of free sulfhydryl groups pre-conjugation, and to verify complete conjugation, respectively.

The following is a preferred protocol for making sulfhydryl-based tumor antigen-carrier protein conjugates in some specific embodiments:
Conjugation of Idiotype/Tumor Antigen to Maleimide-Activated Keyhole Limpet Hemocyanin (KLH)

Keyhole limpet hemocyanin is bound to the heterobifunctional cross-linker sulfosuccinimidyl-4-(N-maleimidomethyl)cyclohexane-1-carboxylate (sulfo-SMCC) via an amine-reactive N-hydroxysuccinimide (NHS) ester. Alternative immunogenic carrier proteins may substitute for KLH in this step.
1. Add 10 μM sulfo-SMCC to 1 μM KLH in 1×PBS pH 7.2 with 1 mM EDTA for a 10-fold molar excess final sulfo-SMCC concentration. The MW for KLH is assumed to be $5\times10^6$ Da, so 1 μM KLH=5 mg/ml. Note: Assume MW for KLH is $5\times10^6$ Da, so 1 μM KLH=5 mg/ml; reaction can be scaled as required.
2. Incubate at room temperature for 1 hour.
3. Remove excess cross-linker with a Zeba desalt spin column (Pierce, Rockford, Ill.), or comparable unit equilibrated with 1×PBS pH 7.2 with 1 mM EDTA (Conjugation buffer).
4. Reduce the Id/tumor antigen in a final concentration of 0.1 mM dithiothreitol (Sigma-Aldrich, St. Louis, Mo.) for 1 hour at 37° C., proceeding immediately to step 5 to prevent re-oxidation of sulfhydryls. Other reducing agents may be substituted at this step to achieve an optimal level of reduction.
5. Dialyze reduced protein into 1×PBS pH 7.2 containing 100 mM EDTA buffer. Note: Conjugations are quality controlled with Ellman's reagent to determine the free sulfhydryl content of the tumor antigen protein pre-reduction, post-reduction, and post-conjugation. (Pierce).
6. Conjugate Id/tumor antigen at a 1:1 ratio of antigen to KLH carrier on a rocker at room temperature for 2 hours.
7. Dialyze conjugates against 1×PBS pH 7.2 at 4° C.
8. Load 10 μg of protein onto a non-reducing SDS-PAGE gel and stain with Coomassie brilliant blue to visually demonstrate complete conjugation of tumor antigen to KLH.
9. Store conjugates at 40 C (short term) or frozen (long term ≥3 days).

Vaccinations.

For tumor challenge experiments, mice were vaccinated with glutaraldehyde or maleimide Id-KLH conjugates (100 μg total: 50 μg Id plus 50 μg KLH) subcutaneously (s.c.) on days −21, −14, and −7 and challenged with tumor on day 0. GM-CSF (55 ng) was co-injected with each Id-KLH vaccine, and injected at the identical site daily for an additional 3 consecutive days with each vaccination as an immune adjuvant (Kwak, L. W., et al., *Proc Natl Acad Sci USA,* 93: 10972-10977, 1996). To treat pre-established tumors, mice were inoculated s.c. on day 0 with tumor and vaccinated with Id-KLH conjugates s.c. as above.

Tumor Challenges.

The A20 and 38C13 tumor cells were washed 3 times and diluted to the appropriate cell concentration in 1× Hank's balanced salt solution (HBSS). Mice were injected with $1\times10^5$ A20 or $5\times10^3$ 38C13 tumor cells s.c. above the base of the tail either one week after the third vaccination (for tumor challenge) or four days before the first vaccination (for therapy of pre-established tumor). Mice were followed for survival and sacrificed when tumors reached 1.4 cm in diameter per institutional guidelines. For BCL-1, cryopreserved tumor cells were prepared by mechanical disruption of a tumor-infiltrated spleen (Timmerman, J. M., et al., *Blood,* 97: 1370-1377., 2001), and enrichment using Lympholyte M gradients (Cedarlane Laboratories Limited, Hornby, Ontario, Canada). Frozen stocks were kept in liquid nitrogen in FCS with 10% DMSO. On the day of tumor challenge, cells were rapidly thawed, washed 3 times, resuspended in 1×HBSS, and immediately injected ($5\times10^4$ cells i.p. per mouse). Mice bearing BCL-1 tumors were sacrificed when they reached a moribund state according to university guidelines.

Quantitation of Anti-Idiotype Antibodies by ELISA.

Mice vaccinated with Id-KLH were bled 4 days before tumor challenge by retro-orbital puncture. For A20 Id, serum samples from individual mice were added to 96-well Nuncimmuno Maxisorp plates (Nunc, Rochester, N.Y.) coated with purified F(ab')$_2$ A20 Id protein (3D6.3, 5 µg/ml) and serially diluted. Anti-Id antibodies were detected by a horse-radish peroxidase (HRP)-conjugated anti-mouse IgG (γ-specific) (Southern Biotech, Birmingham, Ala.). The 1G6 anti-A20 idiotype antibody was used as a standard, or titration curves were compared between vaccinated and control groups. For the IgM-expressing tumors, serum was added to plates coated with 38C13 idiotype protein (38C13-A1.2, 5 µg/ml) or BCL-1 idiotype protein (6A5.1, 5 µg/ml). The S1C5 anti-38C13 Id antibody and B1 anti-BCL-1 idiotype antibodies were used as standards. Absorbance was determined with 2,2'-azinobis(3-ethyl)-benzthiazoline sulfonic acid (ABTS) substrate at 405 nm using a SPECTRAmax Plus 384 microplate reader (Molecular Devices).

Surface Staining of Tumor Cells with Id-KLH Immune Sera.

Washed tumor cells were pre-treated with Fc receptor blocking anti-CD16/CD32 (2.4G2, BD Biosciences, San Jose, Calif.), then incubated with a 1/10 dilution of naïve or immune sera. A20 cells were stained with anti-IgG$_1$-FITC (LO-MG1 Caltag, Burlingame, Calif.) or anti-IgG$_{2b}$-FITC (LO-MG2b Caltag). 38C13 and BCL-1 were stained with anti-IgG-FITC (γ-specific) (Southern Biotech). Appropriate isotype controls were used in all experiments. Cells were washed, fixed with 2% paraformaldehyde, and analyzed using a BD FACScan (BD Biosciences) with FACS Express software (De Novo Software, Thornhill, Ontario, Canada).

Passive Administration of Immune Sera.

BALB/c mice were vaccinated with 100 µg of A20 Id-KLH (maleimide) on days 1, 14, and 28. 55 ng of GM-CSF was given for 4 consecutive days with each vaccination as above. These mice were terminally bled for immune sera collection. Naïve mice were first challenged with $1 \times 10^5$ A20 tumor cells intraperitoneally (i.p.). Eight hours later mice were injected i.p. with 450 µl of immune sera, naïve sera, or HBSS, and animals were followed for survival.

T Cell Depletion Experiments.

Groups of 12 mice were injected with 200 µg of anti-CD4 (GK1.5), anti-CD8α (53.6.72, BALB/c mice), anti-CD8 (HB129, C3H mice), control rat IgG or a control mouse IgG$_{2a}$ (UPC-10) i.p. on days −6, −5, −4, 0, and once every seven days after the day 0 tumor challenge for the duration of the experiment (Syrengelas, A. D. and Levy, R., *J Immunol*, 162: 4790-4795, 1999). T cell depletions were validated by flow cytometry analysis of blood collected from 3 representative mice from each group on day −1. Lymphocytes were stained with anti-CD3-FITC (17A2, BD Biosciences, San Jose, Calif.), anti-CD4-PE (CT-CD4, Caltag, Burlingame, Calif.), and anti-CD8β.2-PE (53-5.8, BD Biosciences, San Jose, Calif.) demonstrating greater than 99% depletion of the target T cell population (data not shown).

Demonstration of Immunoglobulin Cleavage from Maleimide Id-KLH Conjugates.

To demonstrate separation of Id from KLH under physiologic, lysosomal conditions, maleimide and glutaraldehyde Id-KLH conjugates were incubated in 0.5% Triton X-100, 50 mM sodium citrate buffer, pH 4.5, and 2 mM dithiothreitol for 1 hr at room temperature as previously described (Delamarre, L., et al., *Science*, 307: 1630-1634, 2005). Treated proteins, KLH and free Id controls were analyzed on a non-reducing SDS-PAGE gel and stained with coomassie brilliant blue.

Conjugation of Human Immunoglobulins to KLH Using Maleimide.

Mariculture KLH (Pierce) was first bound to the heterobifunctional cross-linker sulfosuccinimidyl-4-(N-maleimidomethyl)cyclohexane-1-carboxylate (sulfo-SMCC) via an amine-reactive N-hydroxysuccinimide (NHS) ester (Pierce). To accomplish this, 10 mM sulfo-SMCC was added to 1 mM KLH (a 10-fold molar excess) in 1 ml of 1×PBS with 1 mM EDTA. The reaction was incubated at room temperature for 1 hour. Excess cross-linker was removed with a Zeba desalt spin column (Pierce, Rockford, Ill.) and the protein was equilibrated in 1×PBS with 100 mM EDTA. Purified human immunoglobulins (polyclonal IgG, monoclonal IgG$_1$, and monoclonal IgG$_3$, Sigma-Aldrich) were reduced using 0.1 mM dithiothreitol (Sigma-Aldrich) for 1 hour at 37° C. and dialyzed into 1×PBS containing 1 mM EDTA buffer to prevent re-oxidation of sulfhydryls. Conjugations were performed at a 1:1 (w:w) ratio of immunoglobulin to KLH on a rocker platform at room temperature for 2 hours, followed by dialysis against 1×PBS. Reactions were quality controlled with Ellman's reagent to determine the free sulfhydryl content of the immunoglobulin protein before and after conjugation. The completeness of the conjugation reaction was assessed by visualizing the proteins via non-reducing SDS-PAGE and staining with coomassie brilliant blue.

Comparison to Glutaraldehybe Id-KLH Vaccine

Maleimide Id-KLH conjugation was compared to glutaraldehyde conjugation in the A20 murine B cell lymphoma model. The method was then validated in the prototypical 38C13 lymphoma model, upon which most current clinical trials are based (Timmerman, J. M. Immunotherapy for lymphomas. *Int J Hematol*, 77: 444-455, 2003). It was found that found that: (1) Maleimide Id-KLH conjugates were strikingly potent in their ability to eradicate A20 lymphoma from tumor-bearing mice, whereas glutaraldehyde Id-KLH had little efficacy; (2) Maleimide Id-KLH elicited both tumor-specific antibodies and T cells, with CD8+ T cells being the major effectors of anti-lymphoma immunity; (3) Maleimide Id-KLH vaccines also showed superior efficacy over glutaraldehyde Id-KLH in the 38C13 and BCL-1 lymphoma models; (4) Standard glutaraldehyde Id-KLH conjugation procedures could result in "over-conjugation" of the tumor antigen, resulting in decreased efficacy; (5) The Id-KLH bond was cleavable in lysosomal conditions only after maleimide conjugation (thio ether bond), and not after glutaraldehyde conjugation; and (6) This conjugation method was easily performed with human immunoglobulins analogous to those used in human Id-KLH vaccine trials. These data support the testing of sulfhydryl-based Id-KLH vaccines in lymphoma clinical trials.

Results: Vaccination with Maleimide-Conjugated Id-KLH Provides Superior Immunity Against A20 Lymphoma Compared with Traditional Glutaraldehyde Id-KLH Conjugate Table 1 is a list of the theoretical rationale for employing a sulfhydryl-based (i.e. maleimide) cross-linking strategy in the preparation of tumor antigen-carrier protein vaccines.

TABLE 1

Comparison of Glutaraldehyde and Maleimide Protein Conjugates

Glutaraldehyde method:

Standard in Id-KLH vaccine production for over 20 years.
Conjugates proteins between lysine, cysteine, tyrosine, and histidine residues.
Permits undesired homotypic cross-linking of two proteins (i.e., KLH-KLH and Id-Id).
Lysine content 6.9 g of per 100 g of KLH.
Extensive cross-linking could destroy or inhibit processing of tumor antigen epitopes.

Maleimide method:

Sulfhydryl-based Id-KLH conjugates not previously evaluated against glutaraldehyde.
Maleimide only conjugates via free sulfhydryl groups found in cysteine residues.
Heterobifunctional strategy permits only formation of the desired Id-KLH linkage.

TABLE 1-continued

Comparison of Glutaraldehyde and Maleimide Protein Conjugates

Cysteine content 1.7 g per 100 g of KLH.
More directed cross-linking may preserve immunogenic tumor antigen epitopes.
Linkage reversible under physiologic conditions found in lysosomes.

Maleimide-conjugated Id-KLH was compared to standard glutaraldehyde Id-KLH in a stringent model of established A20 B cell lymphoma. First, a specific set of conditions for achieving complete conjugation of A20 Id to KLH were established. This involved a controlled, partial reduction of Id with 0.1 mM DTT, immediate transfer to EDTA-containing buffer to preserve reduced sulfhydryl groups, and subsequent reaction with maleimide-activated KLH. This resulted in complete conjugation of Id to KLH, with no free Id detectable by SDS-PAGE, and no insoluble precipitate.

BALB/c mice were injected with a lethal s.c. inoculum of A20 tumor cells, and 4 days later began a series of 3 weekly s.c. immunizations with Id-KLH plus GM-CSF (FIG. 2). Specially, groups of 12 BALB/c mice were innoculated subcutaneously with 1×105 A20 cells on day 0. Mice were vaccinated on days 4, 11 and 18 with 50 µg Id-KLH (conjugated with either maleimide or glutaraldehyde). Each vaccination included 4 consecutive days of 55 ng GM-CSF given in the same location. Mice were sacrificed when tumors reached 1.4 cm in diameter, per institutional protocol. p values represent comparisons between Id-KLH and HBSS (balanced salt solution control) unless otherwise indicated.

As reported previously, glutaraldehyde conjugates of Id-KLH gave no significant protection compared to the HBSS control ($p=0.1434$) (Biragyn, A. and Kwak, L. W. In: A. M. K. J. E. Coligan, D. H. Margulies, E. M. Shevach, W. Strober, and R. Coico, editors. (ed.), *Current Protocols in Immunology*., pp. 20.26.21-20.26.30. Hoboken, N.J.: John Wiley & Sons, Inc., 2001). Maleimide Id-KLH conjugate vaccination eradicated tumor from the majority of mice (58%), in surprising contrast to HBSS control and the glutaraldehyde-conjugated Id-KLH ($p<0.0001$ and $p=0.0004$, respectively). In this specific example, GM-CSF was helpful to the generation of an anti-tumor immune response since mice vaccinated with A20 Id-KLH conjugates without GM-CSF had no significant tumor protection with either the maleimide or glutaraldehyde methods compared to HBSS ($p=0.0937$ and $p=0.0830$, respectively) (data not shown). Id-KLH maleimide and glutaraldehyde conjugate long-term survivors were completely protected against secondary rechallenge with A20 tumor, while naïve mice all succumbed to the tumor challenge (data not shown).

To determine if pre-reduction of the Id protein prior to KLH conjugation was sufficient to render A20 Id more immunogenic, the Id protein was reduced and conjugated to KLH via the maleimide or glutaraldehyde methods. Specifically, groups of 12 BALB/c mice were inoculated subcutaneously with 1×105 A20 cells on day 0. Mice were vaccinated on days 4, 11, and 18 with 50 µg Id-KLH. Each vaccination included 4 consecutive days of 55 ng GM-CSF given in the same location. Reduction of idiotype protein before glutaraldehyde conjugation was performed using the same conditions as for maleimide conjugations. p values represent comparisons between Id-KLH and HBSs.

FIG. 3 shows that Id reduction before glutaraldehyde conjugation to KLH does not enhance the level of tumor eradication compared to a standard glutaraldehyde conjugate (both 25%) ($p=0.93$). The maleimide Id-KLH conjugate once again resulted in significant tumor eradication (66.7%) compared to the reduced and non-reduced glutaraldehyde conjugates ($p=0.010$ and $0.011$, respectively). Thus, the pre-reduction step alone could not enhance the potency of a glutaraldehyde A20 Id-KLH conjugate.

Since maleimide Id-KLH conjugates gave significantly higher levels of tumor eradication than glutaraldehyde Id-KLH, a 50:50 combination of the two conjugates was tested to determine if the anti-tumor immunity could be boosted above what was seen previously with maleimide Id-KLH alone. The maleimide Id-KLH conjugate alone and the combination with an equal amount of glutaraldehyde Id-KLH showed equivalent levels of tumor eradication (58%, FIG. 4). Specifically, groups of 12 BALB/c mice were inoculated subcutaneously with 1×105 A20 cells on day 0. Mice were vaccinated on days 4, 11, and 18 with 50 µg Id-KLH (50 µg maleimide+50 µg glutaraldehyde Id-KLH for mix group). Each vaccination included 4 consecutive days of 55 ng GM-CSF given in the same location. p values represent comparisons between Id-KLH and HBSs.

Both groups vaccinated with maleimide Id-KLH conjugates displayed significantly better survival than the HBSS control ($p=0.0002$). Therefore, maleimide Id-KLH conjugate was sufficient to achieve maximal anti-tumor effects in this model, with no additional immunogenicity contributed by the glutaraldehyde conjugate.

Prophylactic experiments (vaccination followed by tumor challenge) were then conducted in this model to allow assessment of humoral anti-Id immunity. In this setting, anti-Id antibodies are not pulled from the circulation by binding to the surface of growing tumor cells or to circulating free Id protein released from the tumor. Specifically, BALB/c mice were vaccinated subcutaneously on days −28, −21, and −14 with 50 µg Id-KLH. Each vaccination included 4 consecutive days of 55 ng GM-CSF given in the same location. Groups of mice were challenged on day 0 with 2×105 A20 cells subcutaneously. p values represent comparisons between Id-KLH and HBSS unless otherwise indicated. FIG. 5 demonstrates that vaccination before tumor challenge offers significant protection compared to HBSS controls using both maleimide and glutaraldehyde Id-KLH conjugates (58% vs. 25%, $p=0.0077$ and $p<0.0001$, respectively), although protection using maleimide Id-KLH is superior ($p=0.047$).

Serum Anti-Id Antibodies Elicited by Maleimide Id-KLH Vaccination Recognize Native Id on Tumor Cells.

Given that anti-Id antibodies recognize primarily conformational determinants, there was concern that the reduction of cysteine residues prior to maleimide KLH conjugation might alter the folding patterns of the heavy and light chains, with associated loss of important Id epitopes. Serum from the A20 and 38C13 maleimide Id-KLH vaccinated mice was used to stain tumor cells to demonstrate functional binding to the native conformation of Id on the target cells. Sera from mice vaccinated with the A20 Id-KLH conjugate showed substantial tumor cell surface binding by antibodies of the $IgG_1$, but not the $IgG_{2b}$ subclass, FIG. 6A (upper four panels). Antibodies of the $IgG_2$ subclass could not be evaluated with this method since the tumor cell expresses the clonal $IgG_{2a}$ Id on its surface. Similarly, serum from mice vaccinated with maleimide Id-KLH conjugate of the 38C13 lymphoma strongly stained 38C13 cells above background levels compared with naïve sera, indicating recognition of native Id determinants. Thus, the humoral response elicited by maleimide Id-KLH vaccines is highly relevant to native idiotypic determinants expressed on the tumor cell surface.

Mechanisms of Anti-Tumor Immunity After Vaccination with A20 Maleimide Id-KLH.

To determine the role of anti-Id antibodies in the protective immunity against A20, tumor cells were injected into mice i.p. followed by a large dose of immune sera, derived from donor mice vaccinated with A20 maleimide Id-KLH. Specifically, to evaluate the antibody responded generated by Id-KLH vaccinated mice the BALB/c mice from FIG. 5 bleed after the third vaccination 4 days before tumor challenge. 1 μg of immune sera was used to stain A20 cells in vitro for IgG1 (FIG. 6A) or IgG2b (FIG. 6B). Immune sera titers were determined by ELISA (FIG. 6C). As shown in FIG. 6D, the immune sera did not confer any protection or delay in tumor progression compared to naïve sera or HBSS. Specifically, groups of 12 BALB/c mice were innoculated i.p. with 1×105 A20 cells and 8 hours later injected i.p. with 450 μg of Id-KLH (maleimide) immune sera. p values represent comparisons between Id-KLH (glutaraldehye) and Id-KLH (maleimide).

CD8+ T Cells are Important for A20 Tumor Protection after Vaccination with Id-KLH Maleimide Conjugates.

Subsequent studies in A20-bearing mice pre-treated with antibodies to deplete T cell subsets have implicated CD8+ T cells as important for anti-tumor immunity in this particular model (FIG. 7). Specifically, groups of 12 BALB/c mice were inoculated subcutaneously with $1\times10^5$ A20 cells on day 0. Mice were vaccinated on days 4, 11, and 18 with 50 mg Id-KLH. Each vaccination included 4 consecutive days of 55 ng GM-CSF given in the same location. Animals were injected i.p. with 200 μg of 53.6.72 (CD8+), GK1.5 (CD4+), or control rat IgG on days −6, −5, 4, 0, and weekly thereafter. Mice were bleed on day −1 to test for depletion. Mice were sacrificed when tumors reached 1.4 cm in diameter. p values represent comparisons between Id-KLH treated group and HBSS unless otherwise indicated.

Maleimide Id-KLH Conjugates Generate Superior Anti-Id Immunity in the 38C13 Lymphoma Model.

Previous work in the 38C13 B cell lymphoma model has shown that Id-KLH glutaraldehyde can generate protective immunity against tumor challenge, mediated chiefly by anti-Id antibodies (Campbell, M. J., et al., *J Immunol*, 139: 2825-2833, 1987; Campbell, M. J., et al., *J Immunol*, 145: 1029-1036, 1990; Timmerman, J. M. and Levy, R., *J Immunol*, 164: 4797-4803, 2000). This model has served as the prototypical B cell lymphoma in establishing the Id-KLH vaccination strategies now in clinical use (Kaminski, M. S., et al., *J Immunol*, 138: 1289-1296, 1987; Campbell, M. J., et al., *J Immunol*, 139: 2825-2833, 1987; Campbell, M. J., et al., *J Immunol*, 145: 1029-1036, 1990; Campbell, M. J., et al., *J Immunol*, 141: 3227-3233, 1988.; Kwak, L. W., et al., *Proc Natl Acad Sci USA*, 93: 10972-10977, 1996). To determine whether maleimide Id-KLH conjugates could stimulate immune responses comparable to those found with glutaraldehyde Id-KLH conjugates in this tumor system, mice were vaccinated for 3 weeks with Id-KLH complexes and challenged with tumor 7 days later. FIG. 8A shows that the maleimide Id-KLH conjugate protected against tumor at least as well as glutaraldehyde Id-KLH conjugate (p<0.0001 compared to HBSS control). Pooling of data from two replicate experiments demonstrated a significant advantage of maleimide over glutaraldehyde conjugate Id-KLH vaccination in this model (FIG. 8B), (85% vs. 47%, p=0.024).

Since it was previously reported that the major effector mechanism after 38C13 glutaraldehyde Id-KLH vaccination was antibodies (Campbell, M. J., et al., *J Immunol*, 139: 2825-2833, 1987; Campbell, M. J., et al., *J Immunol*, 145: 1029-1036, 1990), immune serum following immunization with maleimide or glutaraldehyde Id-KLH complexes was tested for anti-Id antibodies by ELISA. FIG. 8B shows that the vaccinations with both Id-KLH conjugates elicited anti-Id humoral responses, but that maleimide conjugates induced significantly higher levels compared to that seen after glutaraldehyde Id-KLH (161+/−54 □g/ml vs. 52+/−23 □g/ml, respectively, p<0.0001).

The Duration of Glutaraldehyde Id-KLH Conjugation Significantly Affects the Potency of the Anti-Tumor Immune Response.

In the 38C13 tumor model Id-KLH glutaraldehyde conjugates have been shown to protect some mice against tumor challenge. In current clinical trials, the glutaraldehyde conjugation reaction is typically carried out for 2 hours, regardless of the sensitivity of the individual Id proteins to the cross-linking agent, which is dictated by the amino acid content of the individual tumor Id. It can be theorized that glutaraldehyde cross-linking, as it progressively links not only lysine, but cysteine, tyrosine and histidine residues, might impair the immunogenicity of an Id-KLH conjugate if the reaction proceeds past an optimal timepoint and becomes "overconjugated". The prototypical 38C13 Id was conjugated to KLH with glutaraldehyde for varying lengths of time (0, 2, 15, 30, 60, or 120 minutes), and the resulting conjugates tested for their anti-tumor effects in vivo (FIG. 9A). C3H mice were vaccinated subcutaneously on days −28, −21, and −14 with 50 μg Id-KLH. Each vaccination included 4 consecutive days of 55 ng GM-CSF given in the same location. Groups of 12 mice were challenged on day 0 with 1×103 38C13 cells subcutaneously. The optimal duration of glutaraldehyde Id-KLH conjugation for 38C13 in this experiment was 30 minutes, providing 58% tumor protection (FIG. 9A, 9B). Still, the maleimide Id-KLH conjugate gave the highest proportion of long-term survivors (83%, FIG. 9B). Simply mixing KLH and Id proteins (t=0 minutes) did not elicit any tumor protection compared to the HBSS control. Conjugating the protein for a short time (2 minutes) or a longer time (2 hours) resulted in reduction of tumor protective capacity, with only 42% of mice surviving challenge. The 2 minute, 30 minute, and 2 hour conjugates were statistically better than controls (p=0.0001), but the maleimide Id-KLH conjugate induced statistically better protection than both the 2 minute and 2 hour glutaraldehyde conjugates (p=0.0309 and p=0.0305, respectively). Induced anti-Id antibody titers mirrored the survival results (FIG. 9C). Immune sera titiers were determined by ELISA. p values represent comparisons between Id-KLH (glutaraldehyde) and Id-KLH (maleimmide). Thus, even an optimized glutaraldehyde Id-KLH vaccine could not match the anti-tumor efficacy of maleimide Id-KLH.

Id-KLH Maleimide Conjugations do not Show the Same Time Dependency as Glutaraldehyde Conjugations.

C3H mice were vaccinated subcutaneously on days −28, −21, and −14 with 50 μg Id-KLH. Each vaccination included 4 consecutive days of 55 ng GM-CSF given in the same location. Groups of 12 mice were challenged on day 0 with 1×103 38C13 cells subcutaneously (FIG. 10A). Immune sera titiers were determined by ELISA. P values represent comparisons between Id-KLH treated group and HBSS (FIG. 10B).

CD4+ T Cells Provide Protection Against 38C13.

C3H mice were vaccinated subcutaneously on days −28, −21, and −14 with 50 μg Id-KLH. Each vaccination included 4 consecutive days of 55 ng GM-CSF given in the same location. Groups of 12 mice were challenged on day 0 with $1\times10^3$ 38C13 cells subcutaneously. Animals were injected i.p. with 200 μg of HB129 (CD8+), GK1.5 (CD4+), or control rat IgG on days −6, −5, −4, 0, and weekly thereafter. Mice were bleed on day −1 to test for depletion (FIG. 11).

Groups of 12 BALB/c mice were inoculated i.p. with 10×105 BCL-1 cells on day 0. Mice were vaccinated on days 4, 11, and 18 with 50 mg Id-KLH. Each vaccination included 4 consecutive days of 55 ng GM-CSF given in the same location. Mice were sacrificed when tumors reached 1.4 cm in diameter. p values represent comparisons between Id-KLH treated group and HBSS unless otherwise indicated (FIG. 12A). Groups of 12 BALB/c mice were vaccinated subcutaneously on days −28, −21, and −14 with 50 mg Id-KLH. Each vaccination included 4 consecutive days of 55 ng GM-CSF given in the same location. Mice were bled for immune sera on day −4. The relative levels of anti-BCL-1 antibodies present immune sera was determined by ELISA (FIG. 12B, C).

Id is Cleaved from Maleimide but not Glutaraldehyde Id-KLH Conjugates Under Physiologic Lysosomal Processing Conditions.

Tumor antigen proteins require uptake and proteolytic processing in the lysosomes of antigen presenting cells (APCs) in order to elicit tumor-specific T cell responses (Eisenlohr, L. C. and Rothstein, J. L., Cancer Treat Res, 123: 3-36, 2005). Thus, an optimal Id-KLH vaccine would be one allowing cleavage of the Id protein from the KLH carrier upon uptake by APCs. Whether Id could be cleaved from maleimide conjugates under the physiologically acidic conditions found in lysosomes was determined. Glutaraldehyde or maleimide Id-KLH conjugates were exposed to conditions mimicking the lysosomal processing of antigens (Delamarre, L., et al., Science, 307: 1630-1634, 2005), and the disruption of the different linkages were assessed by SDS-PAGE. FIG. 13A is a visual representation of maleimide Id-KLH conjugate being uptaken and processed by an APC, illustrating the antibody dissociating from KLH after lysosomal fusion. FIG. 13B illustrates that the Id was unable to be cleaved from glutaraldehyde-conjugated Id-KLH, and the high molecular weight complex remained unable to enter the gel, just as for KLH-KLH conjugate. Specifically, 10 mg of each protein was treated with 0.5% Triton X-100, 50 mM sodium citrate buffer, pH 4.5, 2 mM DTT, and 10-20 mg of lysosomal proteins for 1 hour at room temperature. A non-reducing SDS-PAGE gel of lysosomal extract, KLH (glutaraldehyde conjugated), Id-KLH (glutaraldehyde), Id-KLH (maleimide), and idiotype protein was run to visualize release of idiotype from KLH under conditions similar to those seen in lysosomal compartments. In contrast, under these conditions, Id was efficiently cleaved from the maleimide Id-KLH conjugate, indicating the ability of acidic lysosomal conditions to release the tumor antigen for processing and presentation.

The Utility of Ellman's Reagent in Monitoring Free Sulfhydryl Groups During Maleimide Conjugations.

In order to conjugate immunoglobulins or other tumor antigens or other protein antigens to KLH via maleimide, the antigen is first reduced to generate free sulfhydryl groups that can react with the maleimide group on activated KLH to form the stable thio ether bond. Ellman's reagent was used to determine the relative amounts of free sulfhydryl groups in the immunoglobulins pre-reduction, post-reduction, and post-conjugation. FIG. 14A shows a representative experiment in which human IgG1, IgG3, and polyclonal IgG were tested for free sulfhydryl content at various stages to ensure the proper conditions for conjugation to maleimide-activated KLH. Specifically, Human IgG1, IgG3, and polyclonal IgG were tested via Ellman's reagent for the presence of reduced sulfhydryls before reduction, after reduction, and after conjugation to KLH. All three immunoglobulins showed the highest levels of free sulfhydryl residues after reduction, and levels returning to baseline after completion of the conjugation reaction.

Conjugation of Human Immunoglobulins to KLH Using Maleimide.

Current Id-KLH vaccines undergoing phase III clinical testing consist of tumor-specific recombinant IgG1 or IgG3 Id protein, or rescue hybrid-derived IgG or IgM proteins (Hurvitz, S. A. and Timmerman, J. M., Curr Opin Oncol, 17: 432-440, 2005). To demonstrate the potential of the maleimide method for clinical translation, the methods described herein were validated using several preparations of human immunoglobulins. First, unmodified commercial KLH was treated with sulfo-SMCC to yield carrier protein with activated maleimide groups. This was then reacted with pre-reduced monoclonal human IgG1 or polyclonal IgG (FIG. 14B). After conjugation, non-reducing SDS-PAGE analysis revealed complete conjugation of each human Ig to the maleimide-activated KLH (FIG. 14B). More specifically, sulfo-SMCC (Sulfosuccinimidyl-4-(N-maleimidomethyl)cyclohexane-1-carboxylate) was reacted to KLH to form maleimide activated-KLH. This was used to conjugate human IgG1 or polyclonal IgG. The samples were run beside equivalent amounts of unconjugated IgG1 or polyclonal IgG on a non-reducing SDS-PAGE gel to demonstrate the complete conjugation of the antibody to KLH. No free immunoglobulin was seen in the IgG-KLH lanes indicating the immunoglobulin was completely conjugated to the carrier protein, and stable under non-reducing conditions. Thus, human Igs can be efficiently conjugated to KLH for the production of chemically-stable Id-KLH vaccines.

The Effect of DTT Reduction on A20 Idiotype.

3D6.3 (A20 idiotype protein) was reduced for 1 hour at 37° C. in either 0.1 mM or 10 mM DTT. The protein was then conjugated to KLH via an activated maleimide group. Groups of 12 BALB/c mice were inoculated subcutaneously with 1×10$^6$ A20 cells on day 0. Mice were vaccinated on days 4, 11, and 18 with 50 mg Id-KLH. Each vaccination included 4 consecutive days of 55 ng GM-CSF given in the same location. Mice were sacrificed when tumors reached 1.4 cm in diameter, per institutional protocol (FIG. 15A). 3D6.3 was reduced for 1 hour at 37° C. using either 0.1 mM DTT, or 10 mM DTT with subsequent boiling. Ellman's testing was performed on reduced samples (FIG. 15B), Levels of idiotype reduction depend on the type, concentration, and time of treatment with reducing agent. 3D6.3 was reduced for 1 hour at 37° C. using either 0.1 mM DTT, 300 mM DTT (with subsequent boiling, to achieve maximal reduction), or 50 mM 2-Mercaptoethylamine (2-MEA). Ellman's testing was performed on reduced samples. Preferred reducing conditions (0.1 mM DTT or 50 mM 2-MEA) result in only partial reduction of the tumor antigen protein(FIG. 15C).

While the data depicted herein demonstrates efficacy using certain exemplary embodiments of the invention, which are provided for completeness and consistency, it is understood that the invention is not limited to these exemplary embodiments. One of ordinary skill in the art will be readily able to make and use other specific embodiments of the invention consistent with the teachings provided herein.

The technical and scientific terms used herein have the meanings commonly understood by one of ordinary skill in the art to which the present invention pertains, unless otherwise defined. Reference is made herein to various methodologies known to those of skill in the art. Publications and other materials setting forth such known methodologies to which reference is made are incorporated herein by reference in their entirety as though set forth in full. Standard reference works setting forth the general principles of recombinant DNA technology include Sambrook, J., et al., Molecular Cloning,: A Laboratory Manual, 2d Ed., Cold Spring Harbor Laboratory Press, Planview, N.Y. (1989); McPherson, M. J., Ed., Directed Mutagenesis: A Practical Approach, IRL Press, Oxford (1991); Jones, J., Amino Acid and Peptide Synthesis, Oxford Science Publications, Oxford (1992); Austen, B. M. and Westwood, O. M. R., Protein Targeting and Secretion, IRL Press, Oxford (1991). Any suitable materials and/or methods known to those of skill can be utilized in carrying out the present invention; however, preferred materials and/or methods are described. Materials, reagents and the like to which reference is made in the following description and examples are obtainable from commercial sources, unless otherwise noted. It is believed that one skilled in the art can, based on the description herein, utilize the present invention to its fullest extent. The entire contents of all of the references (including literature references, issued patents, published patent applications, and co-pending patent applications) cited throughout this application are hereby expressly incorporated by reference.

What is claimed is:

1. A method of making a cancer vaccine which comprises conjugating an immunogenic carrier comprising keyhole limpet hemocyanin (KLH) with a partially-reduced tumor-specific idiotypic immunoglobulin using a linker comprising a first reactive moiety which is maleimide and a second reactive moiety under conditions which permit the formation of a thio-ether bond between the partially-reduced tumor-specific idiotypic immunoglobulin and the first reactive moiety and a covalent bond between the immunogenic carrier and the second reactive moiety to give the cancer vaccine,
    wherein the thio-ether bond between the linker and the partially-reduced tumor-specific idiotypic immunoglobulin is cleavable under lysosomal processing conditions, and
    wherein the tumor-specific idiotypic immunoglobulin is associated with a B-cell proliferative disease selected from the group consisting of B-cell lymphoma, leukemia, multiple myeloma and light chain amyloidosis.

2. The method according to claim 1, wherein the partially-reduced tumor-specific idiotypic immunoglobulin is obtained using a mild reducing agent selected from the group consisting of dithiothrietol (DTT), 2-mercaptoethanol, and 2-mercaptoethylamine.

3. The method according to claim 1, wherein the partially-reduced tumor-specific idiotypic immunoglobulin is about 50% reduced.

4. The method according to claim 1, wherein the partially-reduced tumor-specific idiotypic immunoglobulin is provided in a solution comprising phosphate-buffered saline and EDTA.

5. The method according to claim 1, wherein the tumor-specific idiotypic immunoglobulin is from a malignant B cell.

6. The method according to claim 5, wherein the tumor-specific idiotypic immunoglobulin is derived from an idiotype-producing hybridoma.

7. The method according to claim 5, wherein the tumor-specific idiotypic immunoglobulin is recombinantly generated using DNA.

8. The method according to claim 1, wherein the efficacy of the vaccine is independent of the duration of the conjugation step.

9. The cancer vaccine made by the method of claim 1.

10. A cancer vaccine comprising a partially-reduced tumor-specific idiotypic immunoglobulin conjugated to an immunogenic carrier comprising keyhole limpet hemocyanin (KLH) by a bifunctional linker having at least one thio-ether bond between a maleimide of the bifunctional linker and the immunogenic carrier or the partially-reduced tumor-specific idiotypic immunoglobulin, wherein the thio-ether bond is cleavable under lysosomal processing conditions, and
    wherein the tumor-specific idiotypic immunoglobulin is associated with a B-cell proliferative disease selected from the group consisting of B-cell lymphoma, leukemia, multiple myeloma and light chain amyloidosis.

11. A method of treating a cancer in a patient which comprises
    administering to the patient a therapeutic amount the cancer vaccine according to claim 10, wherein the cancer is a B-cell proliferative disease.

12. The method according to claim 11, further comprising administering to the patient simultaneously or sequentially an immunologic adjuvant.

13. The method according to claim 12, wherein the adjuvant is selected from the group consisting of GM-CSF, a toll-like receptor (TLR) agonist, poly I:C, and CpG DNA.

14. The method according to claim 11, wherein the cancer expresses one or more tumor-specific idiotypic immunoglobulins.

15. A cancer vaccine which comprises
    a tumor-specific idiotypic immunoglobulin;
    an immunogenic carrier comprising keyhole limpet hemocyanin (KLH);
    a bifunctional linker having a first moiety which is maleimide and a second moiety;
    wherein the tumor-specific idiotypic immunoglobulin is conjugated to the immunogenic carrier by the bifunctional linker, and
    wherein the first moiety forms a thio-ether bond with the tumor-specific idiotypic immunoglobulin or the immunogenic carrier, said thio-ether bond is cleavable under lysosomal processing conditions, and
    wherein the tumor-specific idiotypic immunoglobulin is associated with a B-cell proliferative disease selected from the group consisting of B-cell lymphoma, leukemia, multiple myeloma and light chain amyloidosis.

16. The cancer vaccine of claim 15, wherein the cancer vaccine is effective against a B cell lymphoma in a subject when administered to the subject.

* * * * *